(12) United States Patent
Sutton et al.

(10) Patent No.: US 9,510,945 B2
(45) Date of Patent: *Dec. 6, 2016

(54) MEDICAL DEVICE HANDLE

(71) Applicant: BOSTON SCIENTIFIC SCIMED, INC., Maple Grove, MN (US)

(72) Inventors: Benjamin Sutton, San Jose, CA (US); David J. Paul, Scotts Valley, CA (US); Takashi Ino, San Jose, CA (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 520 days.

This patent is subject to a terminal disclaimer.

(21) Appl. No.: 13/714,927

(22) Filed: Dec. 14, 2012

(65) Prior Publication Data
US 2013/0158655 A1 Jun. 20, 2013

Related U.S. Application Data

(60) Provisional application No. 61/577,845, filed on Dec. 20, 2011.

(51) Int. Cl.
*A61F 2/06* (2013.01)
*A61F 2/24* (2006.01)
(Continued)

(52) U.S. Cl.
CPC ............ *A61F 2/2427* (2013.01); *A61B 17/00* (2013.01); *A61F 2/2436* (2013.01); *A61F 2/962* (2013.01);
(Continued)

(58) Field of Classification Search
CPC ...... A61M 25/01; A61M 25/0147; A61F 2/24; A61F 2/2436; A61F 2/2427; A61F 2/2418; A61F 2002/9517; A61F 2/95; A61F 2/962; A61F 2/2466; A61F 2002/9511;A61F 2002/9528; A61F 2002/9534; A61F 2/1662; A61F 2/1667; A61F 2/167; A61F 2/1672; A61B 17/00; A61B 2017/2946; A61B 2017/00393; A61B 2017/0046; A61B 2017/0042; A61B 17/2841; A61B 17/2909; A61B 2017/2912; A61B 1/0052; A61B 19/22; A61B 17/00234; A61B 2017/291; B25G 1/00–1/10
(Continued)

(56) References Cited

U.S. PATENT DOCUMENTS 3,027,637 A * 4/1962 Seiler ...................... B26B 21/32
30/526
3,241,259 A * 3/1966 McBride ............... F41B 15/022
42/1.08
(Continued)

FOREIGN PATENT DOCUMENTS

CN 1338951 A 3/2002
EP 0512725 A1 11/1992
(Continued)

OTHER PUBLICATIONS

Andersen, H.R. et al. "Transluminal implantation of artificial heart valves. Description of a new expandable aortic valve and initial results with implantation by catheter technique in closed chest pigs." Euro. Heart J. 1992; 13:704-708.
(Continued)

*Primary Examiner* — Amy R Weisberg
(74) *Attorney, Agent, or Firm* — Seager, Tufte & Wickhem LLP

(57) ABSTRACT

A medical device handle may include an elongated handle housing, a rotatable collar disposed about the handle housing, a rotatable control knob disposed about the collar, and a slidable door disposed about the collar. The door may be
(Continued)

rotatably locked to the collar to prevent relative rotation between the door and the collar. The door may slidable from a closed position to a first open position, and slidable from the first open position to a second open position.

14 Claims, 33 Drawing Sheets

(51) Int. Cl.
*A61F 2/962* (2013.01)
*A61B 17/00* (2006.01)
*A61F 2/95* (2013.01)
*A61B 17/29* (2006.01)

(52) U.S. Cl.
CPC *A61B 2017/0042* (2013.01); *A61B 2017/0046* (2013.01); *A61B 2017/00393* (2013.01); *A61B 2017/2946* (2013.01); *A61F 2/2418* (2013.01); *A61F 2/2439* (2013.01); *A61F 2002/9517* (2013.01)

(58) Field of Classification Search
USPC .............. 623/1.11–1.12, 2.11; 606/200, 1; 294/209–210; 81/177.1, 489–491; 16/110.1
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |
| 4,291,420 A | 9/1981 | Reul | |
| 4,326,306 A | 4/1982 | Poler | |
| 4,423,809 A | 1/1984 | Mazzocco | |
| 4,425,908 A | 1/1984 | Simon | |
| 4,501,030 A | 2/1985 | Lane | |
| 4,580,568 A | 4/1986 | Gianturco | |
| 4,602,911 A | 7/1986 | Ahmadi et al. | |
| 4,610,688 A | 9/1986 | Silvestrini et al. | |
| 4,617,932 A | 10/1986 | Kornberg | |
| 4,647,283 A | 3/1987 | Carpentier et al. | |
| 4,648,881 A | 3/1987 | Carpentier et al. | |
| 4,655,218 A | 4/1987 | Kulik et al. | |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,755,181 A | 7/1988 | Igoe | |
| 4,773,420 A * | 9/1988 | Green ................... | A61B 17/11 227/178.1 |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,865,600 A | 9/1989 | Carpentier et al. | |
| 4,872,874 A | 10/1989 | Taheri | |
| 4,909,252 A | 3/1990 | Goldberger | |
| 4,917,102 A | 4/1990 | Miller et al. | |
| 4,954,126 A | 9/1990 | Wallsten | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,064,435 A | 11/1991 | Porter | |
| 5,161,547 A | 11/1992 | Tower | |
| 5,163,953 A | 11/1992 | Vince | |
| 5,209,741 A | 5/1993 | Spaeth | |
| 5,211,086 A * | 5/1993 | Shu ..................... | B25B 15/02 81/58.1 |
| 5,217,483 A | 6/1993 | Tower | |
| 5,258,042 A | 11/1993 | Mehta | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,425,762 A | 6/1995 | Muller | |
| 5,431,676 A | 7/1995 | Dubrul et al. | |
| 5,443,495 A | 8/1995 | Buscemi et al. | |
| 5,443,499 A | 8/1995 | Schmitt | |
| 5,476,506 A | 12/1995 | Lunn | |
| 5,476,510 A | 12/1995 | Eberhardt et al. | |
| 5,480,423 A | 1/1996 | Ravenscroft et al. | |
| 5,484,440 A * | 1/1996 | Allard ................ | A61B 17/8886 128/898 |
| 5,507,767 A | 4/1996 | Maeda et al. | |
| 5,534,007 A | 7/1996 | St. Germain et al. | |
| 5,545,133 A | 8/1996 | Burns et al. | |
| 5,545,211 A | 8/1996 | An et al. | |
| 5,549,665 A | 8/1996 | Vesely et al. | |
| 5,554,185 A | 9/1996 | Block et al. | |
| 5,571,215 A | 11/1996 | Sterman et al. | |
| 5,575,818 A | 11/1996 | Pinchuk | |
| 5,645,559 A | 7/1997 | Hachtman et al. | |
| 5,662,671 A | 9/1997 | Barbut et al. | |
| 5,667,523 A | 9/1997 | Bynon et al. | |
| 5,674,277 A | 10/1997 | Freitag | |
| 5,693,083 A | 12/1997 | Baker et al. | |
| 5,695,498 A | 12/1997 | Tower | |
| 5,713,953 A | 2/1998 | Vallana et al. | |
| 5,716,370 A | 2/1998 | Williamson, IV et al. | |
| 5,720,391 A | 2/1998 | Dohm et al. | |
| 5,733,325 A | 3/1998 | Robinson et al. | |
| 5,735,842 A | 4/1998 | Krueger et al. | |
| 5,769,812 A | 6/1998 | Stevens et al. | |
| 5,800,456 A | 9/1998 | Maeda et al. | |
| 5,807,405 A | 9/1998 | Vanney et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,055 A | 10/1998 | Spiridigliozzi et al. | |
| 5,824,056 A | 10/1998 | Rosenberg | |
| 5,824,064 A | 10/1998 | Taheri | |
| 5,843,158 A | 12/1998 | Lenker et al. | |
| 5,855,597 A | 1/1999 | Jayaraman | |
| 5,855,601 A | 1/1999 | Bessler et al. | |
| 5,860,966 A | 1/1999 | Tower | |
| 5,861,024 A | 1/1999 | Rashidi | |
| 5,861,028 A | 1/1999 | Angell | |
| 5,868,783 A | 2/1999 | Tower | |
| 5,876,448 A | 3/1999 | Thompson et al. | |
| 5,885,228 A | 3/1999 | Rosenman et al. | |
| 5,888,201 A | 3/1999 | Stinson et al. | |
| 5,891,191 A | 4/1999 | Stinson | |
| 5,895,399 A | 4/1999 | Barbut et al. | |
| 5,907,893 A | 6/1999 | Zadno-Azizi et al. | |
| 5,910,154 A | 6/1999 | Tsugita et al. | |
| 5,911,734 A | 6/1999 | Tsugita et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A | 9/1999 | Leonhardt et al. | |
| 5,968,070 A | 10/1999 | Bley et al. | |
| 5,984,957 A | 11/1999 | Laptewicz, Jr. et al. | |
| 5,984,959 A | 11/1999 | Robertson et al. | |

(56) References Cited

U.S. PATENT DOCUMENTS

| | | | |
|---|---|---|---|
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,093,203 A | 7/2000 | Uflacker |
| 6,123,723 A | 9/2000 | Konya et al. |
| 6,142,987 A | 11/2000 | Tsugita |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,171,327 B1 | 1/2001 | Daniel et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,264,647 B1* | 7/2001 | Lechot | A61B 17/1666 606/1 |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,626,892 B1* | 9/2003 | Mayer | A61B 17/062 128/897 |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,746,412 B1* | 6/2004 | Hill | A61M 25/0127 600/585 |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,805,675 B1* | 10/2004 | Gardeski | A61M 25/0136 600/585 |
| 6,814,746 B2 | 11/2004 | Thompson et al. |
| 6,821,282 B2* | 11/2004 | Perry | A61B 17/11 606/1 |
| 6,821,297 B2 | 11/2004 | Snyders |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,855,160 B1* | 2/2005 | Gambale | A61F 2/06 606/108 |
| 6,863,668 B2 | 3/2005 | Gillespie et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak et al. |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |

(56) References Cited

U.S. PATENT DOCUMENTS

| | | | |
|---|---|---|---|
| 7,011,681 B2 | 3/2006 | Vesely | |
| 7,018,406 B2 | 3/2006 | Seguin et al. | |
| 7,025,791 B2 | 4/2006 | Levine et al. | |
| 7,037,331 B2 | 5/2006 | Mitelberg et al. | |
| 7,122,020 B2 | 10/2006 | Mogul | |
| 7,166,097 B2 | 1/2007 | Barbut | |
| 7,175,653 B2 | 2/2007 | Gaber | |
| 7,175,654 B2 | 2/2007 | Bonsignore et al. | |
| 7,189,258 B2 | 3/2007 | Johnson et al. | |
| 7,191,018 B2 | 3/2007 | Gielen et al. | |
| 7,201,772 B2 | 4/2007 | Schwammenthal et al. | |
| 7,235,093 B2 | 6/2007 | Gregorich | |
| 7,258,696 B2 | 8/2007 | Rabkin et al. | |
| 7,318,278 B2 | 1/2008 | Zhang et al. | |
| 7,329,279 B2 | 2/2008 | Haug et al. | |
| 7,374,560 B2 | 5/2008 | Ressemann et al. | |
| 7,381,219 B2 | 6/2008 | Salahieh et al. | |
| 7,445,631 B2 | 11/2008 | Salahieh et al. | |
| 7,632,298 B2 | 12/2009 | Hijlkema et al. | |
| 7,722,666 B2 | 5/2010 | Lafontaine | |
| 8,011,067 B2 * | 9/2011 | Thompson | A61B 1/0052 16/441 |
| 8,157,146 B2 * | 4/2012 | Edoga | A61B 17/068 227/175.1 |
| 8,172,863 B2 * | 5/2012 | Robinson | A61B 17/32002 606/159 |
| 8,241,344 B2 * | 8/2012 | Kusleika | A61F 2/91 623/1.11 |
| 8,663,303 B2 * | 3/2014 | Horvath | A61F 9/00781 623/1.11 |
| 8,721,702 B2 * | 5/2014 | Romoda | A61F 9/00781 604/8 |
| 8,808,350 B2 * | 8/2014 | Schreck | A61F 2/966 623/1.12 |
| 9,131,926 B2 * | 9/2015 | Crisostomo | A61B 17/00 |
| 2001/0039450 A1 | 11/2001 | Pavcnik et al. | |
| 2001/0041928 A1 | 11/2001 | Pavcnik et al. | |
| 2001/0041930 A1 | 11/2001 | Globerman et al. | |
| 2001/0044634 A1 | 11/2001 | Don Michael et al. | |
| 2001/0044652 A1 | 11/2001 | Moore | |
| 2001/0044656 A1 | 11/2001 | Williamson, IV et al. | |
| 2002/0002396 A1 | 1/2002 | Fulkerson | |
| 2002/0010489 A1 | 1/2002 | Grayzel et al. | |
| 2002/0026233 A1 | 2/2002 | Shaknovich | |
| 2002/0029981 A1 | 3/2002 | Nigam | |
| 2002/0032481 A1 | 3/2002 | Gabbay | |
| 2002/0055769 A1 | 5/2002 | Wang | |
| 2002/0058995 A1 | 5/2002 | Stevens | |
| 2002/0077696 A1 | 6/2002 | Zadno-Azizi et al. | |
| 2002/0082609 A1 | 6/2002 | Green | |
| 2002/0095173 A1 | 7/2002 | Mazzocchi et al. | |
| 2002/0095209 A1 | 7/2002 | Zadno-Azizi et al. | |
| 2002/0111674 A1 | 8/2002 | Chouinard et al. | |
| 2002/0120328 A1 | 8/2002 | Pathak et al. | |
| 2002/0151970 A1 | 10/2002 | Garrison et al. | |
| 2002/0161392 A1 | 10/2002 | Dubrul | |
| 2002/0161394 A1 | 10/2002 | Macoviak et al. | |
| 2002/0177766 A1 | 11/2002 | Mogul | |
| 2002/0188341 A1 | 12/2002 | Elliott | |
| 2002/0188344 A1 | 12/2002 | Bolea et al. | |
| 2003/0023303 A1 | 1/2003 | Palmaz et al. | |
| 2003/0036791 A1 | 2/2003 | Philipp et al. | |
| 2003/0040771 A1 | 2/2003 | Hyodoh et al. | |
| 2003/0040772 A1 | 2/2003 | Hyodoh et al. | |
| 2003/0040791 A1 | 2/2003 | Oktay | |
| 2003/0050694 A1 | 3/2003 | Yang et al. | |
| 2003/0055495 A1 | 3/2003 | Pease et al. | |
| 2003/0060844 A1 | 3/2003 | Borillo et al. | |
| 2003/0070944 A1 | 4/2003 | Nigam | |
| 2003/0109924 A1 | 6/2003 | Cribier | |
| 2003/0109930 A1 | 6/2003 | Bluni et al. | |
| 2003/0114912 A1 | 6/2003 | Sequin et al. | |
| 2003/0125795 A1 | 7/2003 | Pavcnik et al. | |
| 2003/0130729 A1 | 7/2003 | Paniagua et al. | |
| 2003/0135257 A1 | 7/2003 | Taheri | |
| 2003/0144732 A1 | 7/2003 | Cosgrove et al. | |
| 2003/0149476 A1 | 8/2003 | Damm et al. | |
| 2003/0149478 A1 | 8/2003 | Figulla et al. | |
| 2003/0176884 A1 | 9/2003 | Berrada et al. | |
| 2003/0181850 A1 | 9/2003 | Diamond et al. | |
| 2003/0187495 A1 | 10/2003 | Cully et al. | |
| 2003/0199913 A1 | 10/2003 | Dubrul et al. | |
| 2003/0199971 A1 | 10/2003 | Tower et al. | |
| 2003/0199972 A1 | 10/2003 | Zadno-Azizi et al. | |
| 2003/0208224 A1 | 11/2003 | Broome | |
| 2003/0212429 A1 | 11/2003 | Keegan et al. | |
| 2003/0212452 A1 | 11/2003 | Zadno-Azizi et al. | |
| 2003/0212454 A1 | 11/2003 | Scott et al. | |
| 2003/0216774 A1 | 11/2003 | Larson | |
| 2003/0225445 A1 | 12/2003 | Derus et al. | |
| 2003/0229390 A1 | 12/2003 | Ashton et al. | |
| 2003/0233117 A1 | 12/2003 | Adams et al. | |
| 2004/0034411 A1 | 2/2004 | Quijano et al. | |
| 2004/0039436 A1 | 2/2004 | Spenser et al. | |
| 2004/0049224 A1 | 3/2004 | Buehlmann et al. | |
| 2004/0049226 A1 | 3/2004 | Keegan et al. | |
| 2004/0049262 A1 | 3/2004 | Obermiller et al. | |
| 2004/0073198 A1 | 4/2004 | Gilson et al. | |
| 2004/0082904 A1 | 4/2004 | Houde et al. | |
| 2004/0082967 A1 | 4/2004 | Broome et al. | |
| 2004/0087982 A1 | 5/2004 | Eskuri | |
| 2004/0088045 A1 | 5/2004 | Cox | |
| 2004/0093016 A1 | 5/2004 | Root et al. | |
| 2004/0098022 A1 | 5/2004 | Barone | |
| 2004/0098099 A1 | 5/2004 | McCullagh et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0127979 A1 | 7/2004 | Wilson et al. | |
| 2004/0133274 A1 | 7/2004 | Webler et al. | |
| 2004/0138694 A1 | 7/2004 | Tran et al. | |
| 2004/0138742 A1 | 7/2004 | Myers et al. | |
| 2004/0148021 A1 | 7/2004 | Cartledge et al. | |
| 2004/0153094 A1 | 8/2004 | Dunfee et al. | |
| 2004/0158277 A1 | 8/2004 | Lowe et al. | |
| 2004/0167565 A1 | 8/2004 | Beulke et al. | |
| 2004/0181140 A1 | 9/2004 | Falwell et al. | |
| 2004/0186563 A1 | 9/2004 | Lobbi | |
| 2004/0204755 A1 | 10/2004 | Robin | |
| 2004/0215331 A1 | 10/2004 | Chew et al. | |
| 2004/0215339 A1 | 10/2004 | Drasler et al. | |
| 2004/0220655 A1 | 11/2004 | Swanson et al. | |
| 2004/0225321 A1 | 11/2004 | Krolik et al. | |
| 2004/0254636 A1 | 12/2004 | Flagle et al. | |
| 2005/0033402 A1 | 2/2005 | Cully et al. | |
| 2005/0043711 A1 | 2/2005 | Corcoran et al. | |
| 2005/0075662 A1 | 4/2005 | Pedersen et al. | |
| 2005/0085841 A1 | 4/2005 | Eversull et al. | |
| 2005/0085842 A1 | 4/2005 | Eversull et al. | |
| 2005/0085843 A1 | 4/2005 | Opolski et al. | |
| 2005/0085890 A1 | 4/2005 | Rasmussen et al. | |
| 2005/0090834 A1 * | 4/2005 | Chiang | A61F 2/07 606/108 |
| 2005/0090846 A1 | 4/2005 | Pedersen et al. | |
| 2005/0096692 A1 | 5/2005 | Linder et al. | |
| 2005/0096734 A1 | 5/2005 | Majercak et al. | |
| 2005/0096735 A1 | 5/2005 | Hojeibane et al. | |
| 2005/0096736 A1 | 5/2005 | Osse et al. | |
| 2005/0096738 A1 | 5/2005 | Cali et al. | |
| 2005/0100580 A1 | 5/2005 | Osborne et al. | |
| 2005/0107822 A1 | 5/2005 | WasDyke | |
| 2005/0113910 A1 | 5/2005 | Paniagua et al. | |
| 2005/0137686 A1 | 6/2005 | Salahieh et al. | |
| 2005/0137687 A1 | 6/2005 | Salahieh et al. | |
| 2005/0137688 A1 | 6/2005 | Salahieh et al. | |
| 2005/0137689 A1 | 6/2005 | Salahieh et al. | |
| 2005/0137691 A1 | 6/2005 | Salahieh et al. | |
| 2005/0137692 A1 | 6/2005 | Haug et al. | |
| 2005/0137694 A1 | 6/2005 | Haug et al. | |
| 2005/0137695 A1 | 6/2005 | Salahieh et al. | |
| 2005/0137696 A1 | 6/2005 | Salahieh et al. | |
| 2005/0137697 A1 | 6/2005 | Salahieh et al. | |

(56) References Cited

U.S. PATENT DOCUMENTS

| | | |
|---|---|---|
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0165477 A1 | 7/2005 | Anduiza et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster |
| 2005/0203615 A1 | 9/2005 | Forster |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2007/0244555 A1* | 10/2007 | Rafiee ............... A61F 2/2445 623/2.11 |
| 2007/0288089 A1 | 12/2007 | Gurskis et al. |
| 2008/0082165 A1 | 4/2008 | Wilson et al. |
| 2008/0109059 A1* | 5/2008 | Gordon ............. A61B 17/3468 623/1.11 |
| 2008/0114435 A1* | 5/2008 | Bowe ................. A61F 2/95 623/1.11 |
| 2008/0125859 A1 | 5/2008 | Salahieh et al. |
| 2008/0154244 A1* | 6/2008 | Singh ............... A61B 17/4241 606/1 |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255542 A1* | 10/2008 | Nimgaard ............ A61F 2/95 604/535 |
| 2008/0255588 A1 | 10/2008 | Hinman |
| 2008/0288054 A1 | 11/2008 | Pulnev et al. |
| 2009/0005863 A1 | 1/2009 | Goetz et al. |
| 2009/0018507 A1* | 1/2009 | Schmitz ............ A61B 17/3401 604/164.03 |
| 2009/0054969 A1 | 2/2009 | Salahieh et al. |
| 2009/0076598 A1 | 3/2009 | Salahieh et al. |
| 2009/0171456 A1 | 7/2009 | Kveen et al. |
| 2009/0222076 A1 | 9/2009 | Figulla et al. |
| 2009/0254165 A1* | 10/2009 | Tabor ................ A61F 2/2412 623/1.11 |
| 2009/0264759 A1 | 10/2009 | Byrd |
| 2009/0264997 A1 | 10/2009 | Haug et al. |
| 2009/0326566 A1* | 12/2009 | Alvarado ........... A61B 17/0469 606/153 |
| 2010/0010293 A1* | 1/2010 | Sato .................. A61F 2/88 600/101 |
| 2010/0030237 A1* | 2/2010 | Hayashi ............ A61B 17/0401 606/144 |
| 2010/0030255 A1* | 2/2010 | Berra ................ A61F 2/07 606/200 |
| 2010/0049313 A1* | 2/2010 | Alon ................. A61F 2/2418 623/2.11 |
| 2010/0121434 A1* | 5/2010 | Paul ................. A61F 2/2436 623/2.11 |
| 2010/0191326 A1 | 7/2010 | Alkhatib |
| 2010/0217274 A1* | 8/2010 | Lee .................. A61F 2/1672 606/107 |
| 2010/0219092 A1 | 9/2010 | Salahieh et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1* | 9/2010 | Zhang ............... A61F 2/2418 623/2.11 |
| 2010/0256725 A1* | 10/2010 | Rasmussen ......... A61F 2/07 623/1.11 |
| 2010/0256727 A1* | 10/2010 | Gerdts ............... A61F 2/95 623/1.11 |
| 2010/0274340 A1* | 10/2010 | Hartley ............. A61F 2/95 623/1.11 |
| 2010/0280495 A1 | 11/2010 | Paul et al. |
| 2010/0286768 A1 | 11/2010 | Alkhatib |
| 2011/0015728 A1 | 1/2011 | Jimenez et al. |
| 2011/0054585 A1* | 3/2011 | Osborne ............ A61F 2/95 623/1.11 |
| 2011/0087066 A1 | 4/2011 | Boutillette et al. |
| 2011/0088519 A1* | 4/2011 | Hu .................. B25H 3/003 81/63.1 |
| 2011/0202128 A1 | 8/2011 | Duffy |
| 2011/0208296 A1* | 8/2011 | Duffy ............... A61F 2/2427 623/2.11 |
| 2011/0251683 A1 | 10/2011 | Tabor |
| 2011/0257718 A1* | 10/2011 | Argentine ........... A61F 2/966 623/1.11 |
| 2011/0264074 A1* | 10/2011 | Tegg ................ A61B 8/12 604/523 |
| 2011/0264199 A1 | 10/2011 | Tran et al. |
| 2011/0264204 A1 | 10/2011 | Khairkhahan |
| 2011/0270372 A1* | 11/2011 | Argentine .......... A61F 2/95 623/1.11 |
| 2011/0282425 A1* | 11/2011 | Dwork .............. A61F 2/95 623/1.11 |
| 2011/0295216 A1* | 12/2011 | Miller .............. A61F 2/95 604/264 |
| 2011/0307049 A1* | 12/2011 | Kao ................. A61F 2/966 623/1.11 |
| 2012/0016468 A1 | 1/2012 | Robin et al. |
| 2012/0035717 A1* | 2/2012 | Duffy ............... A61F 2/2427 623/2.11 |
| 2012/0041547 A1* | 2/2012 | Duffy ............... A61F 2/2436 623/2.11 |
| 2012/0078076 A1* | 3/2012 | Stewart ............. A61B 18/1492 600/373 |
| 2012/0103840 A1 | 5/2012 | McCaffrey |
| 2012/0136425 A1* | 5/2012 | Orr ................. A61F 2/95 623/1.11 |
| 2012/0172968 A1* | 7/2012 | Chuter .............. A61F 2/95 623/1.12 |
| 2012/0239142 A1 | 9/2012 | Liu et al. |
| 2012/0245606 A1* | 9/2012 | Goldberg ........... A61B 17/11 606/153 |
| 2012/0271398 A1 | 10/2012 | Essinger et al. |
| 2012/0290066 A1* | 11/2012 | Nabulsi ............. A61F 2/966 623/1.11 |
| 2012/0296407 A1* | 11/2012 | Caselnova .......... A61F 2/962 623/1.11 |
| 2012/0305441 A1 | 12/2012 | Murray et al. |
| 2012/0310332 A1 | 12/2012 | Murray et al. |
| 2013/0123757 A1* | 5/2013 | Crisostomo ........ A61B 17/00 606/1 |

(56) References Cited

U.S. PATENT DOCUMENTS

| | | | |
|---|---|---|---|
| 2013/0123796 A1* | 5/2013 | Sutton | A61B 17/00234 606/108 |
| 2013/0123898 A1* | 5/2013 | Tung | A61F 2/966 623/1.11 |
| 2013/0123912 A1* | 5/2013 | Tung | A61F 2/2427 623/2.11 |
| 2013/0131774 A1* | 5/2013 | Nabulsi | A61F 2/95 623/1.11 |
| 2013/0144276 A1* | 6/2013 | Crisostomo | A61B 17/00 606/1 |
| 2013/0158653 A1* | 6/2013 | Gamarra | A61F 2/2436 623/2.11 |

FOREIGN PATENT DOCUMENTS

| | | |
|---|---|---|
| EP | 0409929 B1 | 4/1997 |
| EP | 1000590 A1 | 5/2000 |
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1229864 B1 | 4/2005 |
| EP | 1430853 A2 | 6/2005 |
| EP | 1059894 B1 | 7/2005 |
| EP | 1078610 B1 | 8/2005 |
| EP | 1576937 A2 | 9/2005 |
| EP | 1582178 A2 | 10/2005 |
| EP | 1582179 A2 | 10/2005 |
| EP | 1600121 A1 | 11/2005 |
| EP | 1156757 B1 | 12/2005 |
| EP | 1616531 A2 | 1/2006 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9836790 A1 | 8/1998 |
| WO | 9850103 A1 | 11/1998 |
| WO | 9857599 A2 | 12/1998 |
| WO | 9905975 A1 | 2/1999 |
| WO | 9944542 A2 | 9/1999 |
| WO | 0009059 A2 | 2/2000 |
| WO | 0044308 A2 | 8/2000 |
| WO | 0044313 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0164137 A1 | 9/2001 |
| WO | 0236048 A1 | 5/2002 |
| WO | 0239910 A2 | 5/2002 |
| WO | 0241789 A2 | 5/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03030776 A2 | 4/2003 |
| WO | 03094797 A1 | 11/2003 |
| WO | 2004014256 A1 | 2/2004 |
| WO | 2004019811 A2 | 3/2004 |
| WO | 2004019825 A1 | 3/2004 |
| WO | 2004023980 A2 | 3/2004 |
| WO | 2004026117 A2 | 4/2004 |
| WO | 2004041126 A1 | 5/2004 |
| WO | 2004047681 A1 | 6/2004 |
| WO | 2004066876 A1 | 8/2004 |
| WO | 2004082536 A1 | 9/2004 |
| WO | 2005084595 A1 | 9/2005 |
| WO | 2005087140 A1 | 9/2005 |

OTHER PUBLICATIONS

Atwood, A. et al. "Insertion of Heart Valves by Catheterization." Project Supervised by Prof. S. Mutfu of Northeaster University 2001-2002:36-40.

Bodnar, E. et al. Replacement Cardiac Valves R Chapter 13: Extinct cardiac valve prostheses. Pergamon Publishing Corporation. New York, 1991: 307-322.

Boudjemline, Y et al. Percutaneous implantation of a biological valve in the aorta to treat aortic valve insufficiency—a sheep study. Med Sci. Monit. 2002; vol. 8, No. 4: BR 113-116.

Boudjemline, Y et al. "Percutaneous implantation of a valve in the descending aorta in lambs." Euro. Heart J. 2002; 23: 1045-1049.

Boudjemline, Y et al. "Percutaneous pulmonary valve replacement in a large right ventricular outflow tract: an experimental study." Journal of the American College of Cardiology. 2004; vol. 43(6): 1082-1087.

Boudjemline, Y et al. "Percutaneous valve insertion: A new approach?" J. of Thoracic and Cardio. Surg. 2003; 125(3): 741-743.

Boudjemline, Y et al. "Steps Toward Percutaneous Aortic Valve Replacement." Circulation. 2002; 105 775-778.

Cribier, A et al. "Early Experience with Percutaneous Transcatheter Implantation of Heart Valve Prosthesis for the Treatment of End-Stage Inoperable Patients with Calcific Aortic Stenosis." Journal of the American College of Cardiology. 2004; 43(4): 698-703.

Cribier, A et al. "Percutaneous Transcatheter Implantation of a Aortic Valve Prosthesis for Calcific Aortic Stenosis: First Human Case Description." Circulation. 2002; 106:3006-3008.

Cribier, A et al. "Percutaneous Transcatheter Implantation of an Aortic Valve Prosthesis for Calcific Aortic Stenosis: First Human Case." Percutaneous Valve Technologies, Inc. 2002: 16 pages.

Ferrari, M et al. "Percutaneous transvascular aortic valve replacement with self expanding stent-valve device." Poster from the presentation given at SMIT 2000, 12th International Conference. Sep. 5, 2000.

Hijazi, Z.M. "Transcatheter Valve Replacement: A New Era of Percutaneous Cardiac Intervention Begins." Journal of the American College of Cardiology 2004; 43(6): 1088-1089.

Huber, C.H. et al. "Do valved stents compromise coronary flow?" European Journal of Cardio-thoracic Surgery. 2004; vol. 25: 754-759.

Knudsen, L.L. et al. "Catheter-implanted prosthetic heart valves." Int'l Journal of Art. Organs. 1993; 16(5): 253-262.

Kort, S et al. "Minimally invasive aortic valve replacement: Echocardiographic and clinical results." American Heart Journal. 2001; 142(3): 476-481.

Love, C et al. "The Autogenous Tissue Heart Valve: Current Status." Journal of Cardiac Surgery. 1991; 6(4): 499-507.

Lutter, G et al. "Percutaneous aortic valve replacement: An experimental study. I. Studies on implantation." Journal of Thoracic and Cardio. Surgery. 2002; 123(4): 768-776.

Moulopoulos, S.D. et al. "Catheter-Mounted Aortic Valves." Annals of Thoracic Surgery. 1971; 11(5): 423-430.

Paniagua, D et al. "Percutaneous heart valve in the chronic in vitro testing model." Circulation. 2002; 106: e51-e52.

Paniagua, D et al. Heart Watch (2004). Texas Heart Institute. Spring, 2004 Edition: 8 pages.

Pavcnik, D et al. "Percutaneous bioprosthetic veno valve: A long-term study in sheep." Journal of Vascular Surgery. 2002; 35(3): 598-603.

Phillips, S.J. et al. "A Temporary Catheter-Tip Aortic Valve: Hemodynamic Effects on Experimental Acute Aortic Insufficiency." Annals of Thoracic Surgery. 1976; 21(2): 134-136.

Sochman, J. et al. "Percutaneous Transcatheter Aortic Disc Valve Prosthesis Implantation: A Feasibility Study." CardioVascular Interventional Radiology. 2000; 23: 384-388.

Stuart, M. "In Heart Valves, A Brave, New Non-Surgical World." Start-Up. 2004: 9-17.

(56) References Cited

OTHER PUBLICATIONS

Vahanian, A. et al. "Percutaneous Approaches to Valvular Disease." Circulation. 2004; 109: 1572-1579.
Van Herwerden, L. A. et al. "Percutaneous valve implantation: back to the future?" European Heart Journal. 2002; 23(18): 1415-1416.
Zhou, J. Q. et al. "Self-expandable valved stent of large size: off-bypass implantation in pulmonary position." European Journal of Cardio-thoracic Surgery. 2003; 24: 212-216.
Paul et al. U.S. Appl. No. 12/578,463 entitled "Medical Devices and Delivery Systems for Delivering Medical Devices," filed Oct. 13, 2009.

* cited by examiner

MEDICAL DEVICE HANDLE

BACKGROUND

Medical devices typically used for cardiovascular system treatments may involve complex and invasive therapies resulting is significant discomfort, pain, and long recovery times for patients. Recently, less invasive, percutaneous treatments have been developed. There is an ongoing need for improved, less invasive cardiovascular treatments.

SUMMARY

A medical device handle may comprise an elongated handle housing having a radially-extending transverse ridge disposed about its circumference, a rotatable collar disposed about a proximal portion of the handle housing, a distal end of the collar abutting a proximally-facing surface of the ridge, a rotatable control knob disposed at a proximal end of the handle housing, and a slidable door disposed about a distal portion of the collar. The door may be rotatably locked to the collar to prevent relative rotation therebetween. The door may slidable from a closed position to a first open position, and further slidable from the first open position to a second open position.

BRIEF DESCRIPTION OF THE DRAWINGS

The invention may be more completely understood in consideration of the following detailed description of various embodiments of the invention in connection with the accompanying drawings, in which.

Figure 1:
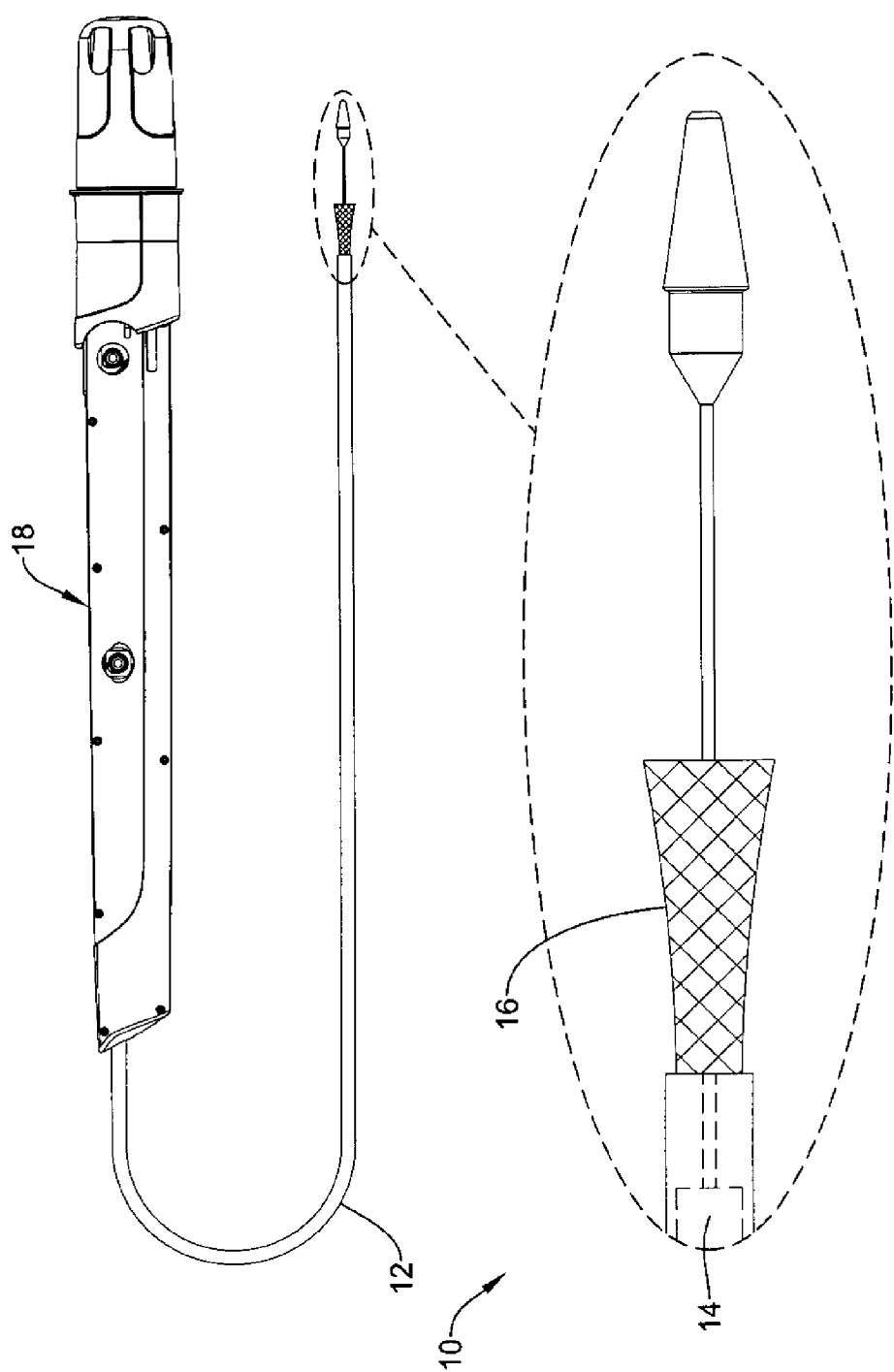
FIG. 1 is side view of an example medical device system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 is a side view of an example medical device system 10. It should be noted that some features of system 10 are either not shown, or are shown schematically, in FIG. 1 for simplicity. Additional details regarding some of the components of system 10 are provided in other figures in greater detail. System 10 may be used to deliver and/or deploy a variety of medical devices to a number of locations within the anatomy. In at least some embodiments, system 10 is a replacement heart valve delivery system (e.g., a replacement aortic valve delivery system) that can be used for percutaneous delivery of a replacement heart valve. This, however, is not intended to be limiting as system 10 may also be used for other interventions including mitral valve replacement, valve repair, valvuloplasty, and the like, or other similar interventions.

System 10 may generally be described as a catheter system that includes an outer sheath or catheter 12 and an inner catheter or tube 14 (a portion of which is shown in FIG. 1 in phantom line) extending at least partially through outer sheath 12. A medical device implant 16 may be coupled to inner catheter 14 and disposed within outer sheath 12 during delivery of implant 16. A handle 18 may be disposed at the proximal end of outer sheath 12 and inner catheter 14. In general, handle 18 may be configured to manipulate the position of outer sheath 12 relative to inner catheter 14 as well as aid in the deployment of implant 16.

In use, system 10 may be advanced percutaneously through the vasculature to a position adjacent to an area of interest. For example, system 10 may be advanced through the vasculature to a position adjacent to a defective aortic valve. During delivery, implant 16 may be generally disposed in an elongated and low profile "delivery" configuration within outer sheath 12. Once positioned, outer sheath 12 may be refracted to expose implant 16. Implant 16 may be actuated in order to expand implant into a generally shortened and larger profile "deployed" configuration suitable for implantation within the anatomy. When implant 16 is suitably deployed within the anatomy, system 10 can be removed from the vasculature, leaving implant 16 in place to function as, for example, a suitable replacement for the native aortic valve. In at least some interventions, implant 16 may be deployed within the native valve (e.g., the native valve is left in place and not excised). Alternatively, the native valve may be removed and implant 16 may be deployed in its place as a replacement.

Figure 2:
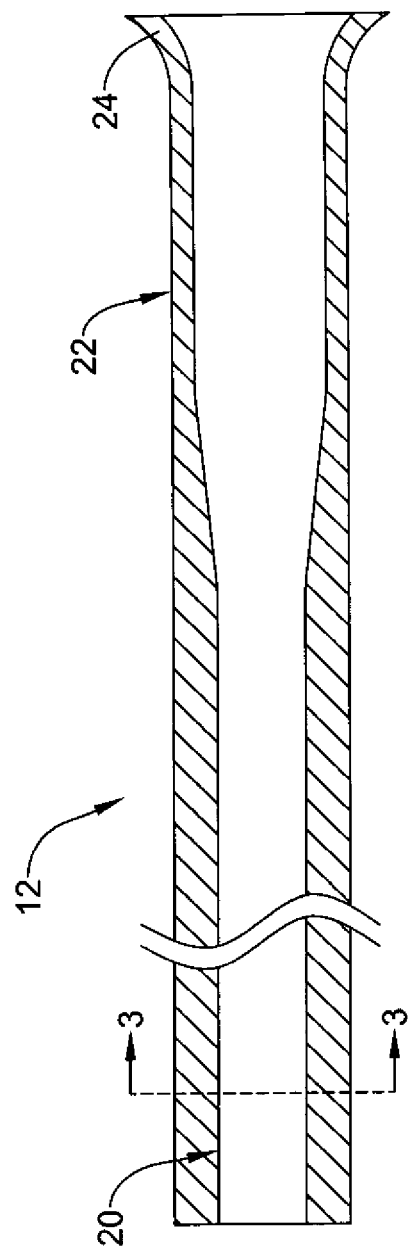
FIG. 2 is a cross-sectional side view of an example outer sheath.

FIGS. 2-13 (as well as other figures) illustrate some of the components of system 10. For example, FIG. 2 is a cross-sectional side view of outer sheath 12. Here it can be seen that outer sheath 12 has a proximal portion 20 and a distal portion 22. Distal portion 22 may have a slightly enlarged or flared inner diameter, which may provide additional space for holding implant 16 therein. For example, the inner diameter of outer sheath 12 along proximal portion 20 may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.56388±0.0508 cm (0.222±0.002 inches). The inner diameter of outer sheath 12 along distal portion 22 may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.579 to 0.5842 cm (0.228 to 0.230 inches). At the distal end of distal portion 22 may be a distal tip 24, which may be flared or otherwise have a funnel-like shape. The funnel-like shape increases the outer diameter (and inner diameter) of outer sheath 12 at distal tip 24 and may aid in the sheathing and/or re-sheathing of implant 16 into outer sheath 12. Other than at distal tip 24, outer sheath 12 may have a generally constant outer diameter. For example, outer sheath 12 may have an outer diameter in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.6858 cm (0.270 inches). These are just examples. Other embodiments are contemplated that have differing dimensions (including those appropriate for differently sized patients including children) and/or arrangements for the outer diameter and/or inner diameter of outer sheath 12. These contemplated embodiments include outer sheaths with flared or otherwise variable outer diameters, embodiments with constant inner diameters, combinations thereof, and the like. Outer sheath 12 may also have a length that is appropriate for reaching the intended area of interest within the anatomy. For example, outer sheath 12 may have a length in the range of about 30 to 200 cm, or about 60 to 150 cm, or about 100 to 120 cm, or about 108±0.20 cm. Outer sheath 12 may also be curved. For example, a distal section of outer sheath 12 may be curved. In one example, the radius of the curve (measured from the center of outer sheath 12) may be in the range of about 2 to 6 cm (20 to 60 mm), or about 3 to 4 cm (30 to 40 mm), or about 3.675 cm (36.75 mm). Again, these dimensions are examples and are not intended to be limiting.

Figure 3:
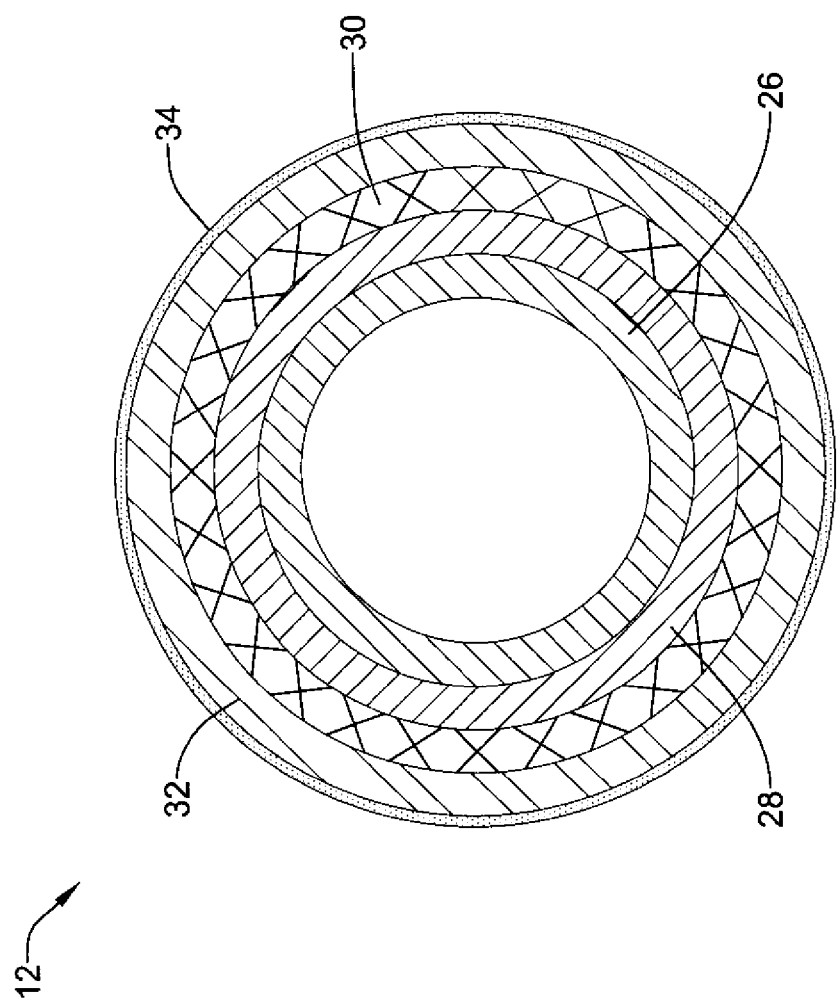
FIG. 3 is a transverse cross-sectional view taken through line 3-3 in FIG. 2.

Outer sheath 12 may be formed from a singular monolithic tube or unitary member. Alternatively, outer sheath 12 may include a plurality of layers or portions. One or more of these layers may include a reinforcing structure such as a braid, coil, mesh, combinations thereof, or the like. FIG. 3 illustrates one example of a multilayer structure for outer sheath 12. For example, outer sheath 12 may include an inner liner or layer 26. An intermediate or tier layer 28 may be disposed on inner liner 26. A reinforcement 30 may be disposed on intermediate layer 28. A topcoat or outer layer 32 may be disposed on reinforcement 30. Finally, an outer coating 34 (e.g., a lubricious coating, a hydrophilic coating, a hydrophobic coating, etc.) may be disposed along portions or all of topcoat 32. These are just examples. Several alternative structural configurations are contemplated for outer sheath 12 including embodiments including two or more layers that may be different from those shown in FIG. 3, embodiments without a reinforcement, and the like, or other suitable configurations.

The dimensions and materials utilized for the various layers of outer sheath 12 may also vary. For example, inner liner 26 may include a polymeric material such as fluorinated ethylene propylene (FEP) and may have a thickness in the range of about 0.00254 to 0.0127 cm (0.001 to 0.005 inches) or about 0.00762±0.00254 (0.003±0.001 inches), intermediate layer 28 may include a polymer material such as polyether block amide (e.g., PEBAX 6333) and may have a thickness in the range of about 0.00254 to 0.0127 cm (0.001 to 0.005 inches) or about 0.00508±0.00254 (0.002±0.001 inches), outer coating 34 may include a polymer material such as polyether block amide (e.g., PEBAX 7233) and may have a thickness in the range of about 0.00254 to 0.0254 cm (0.001 to 0.01 inches). In some embodiments, outer coating 34 may vary in thickness. For example, along proximal portion 20 outer coating 34 may have greater thickness, such as about 0.0127 to about 0.0508 cm or about 0.02159 cm (0.005 to 0.02 inches or about 0.0085 inches), than along distal portion 22 and/or distal tip 24, which may be about 0.0127 to about 0.0508 cm or about 0.01651 cm (e.g., about 0.005 to 0.02 inches or about 0.0065 inches). These are just examples as other suitable materials may be used.

The form of distal tip 24 may also vary. For example, in at least some embodiments, inner liner 26 (i.e., a 2.5 mm section thereof) may be extended up and around the distal end of outer sheath 12 (e.g., around reinforcement 30 and topcoat 32). A ring member (not shown) made from a suitable material such as a 55D polyether block amide (e.g., 55D PEBAX) may be disposed over inner liner 26 and heat bonded to form distal tip 24. This may form the funnel-like shape of distal tip 24.

Reinforcement 30 may also vary in form. In at least some embodiments, reinforcement 30 may take the form of a braid, coil, mesh, or the like. For example, in some embodiments, reinforcement 30 may include a metallic braid (e.g., stainless steel). In some of these embodiments, reinforcement 30 may also include additional structures such as one or more longitudinally-extending strands. For example, reinforcement 30 may include a pair of longitudinally-extending aramid and/or para aramid strands (for example, KEVLAR®) disposed on opposite sides of the braid. These strands may or may not be woven into portions or all of the braid.

Figure 4:
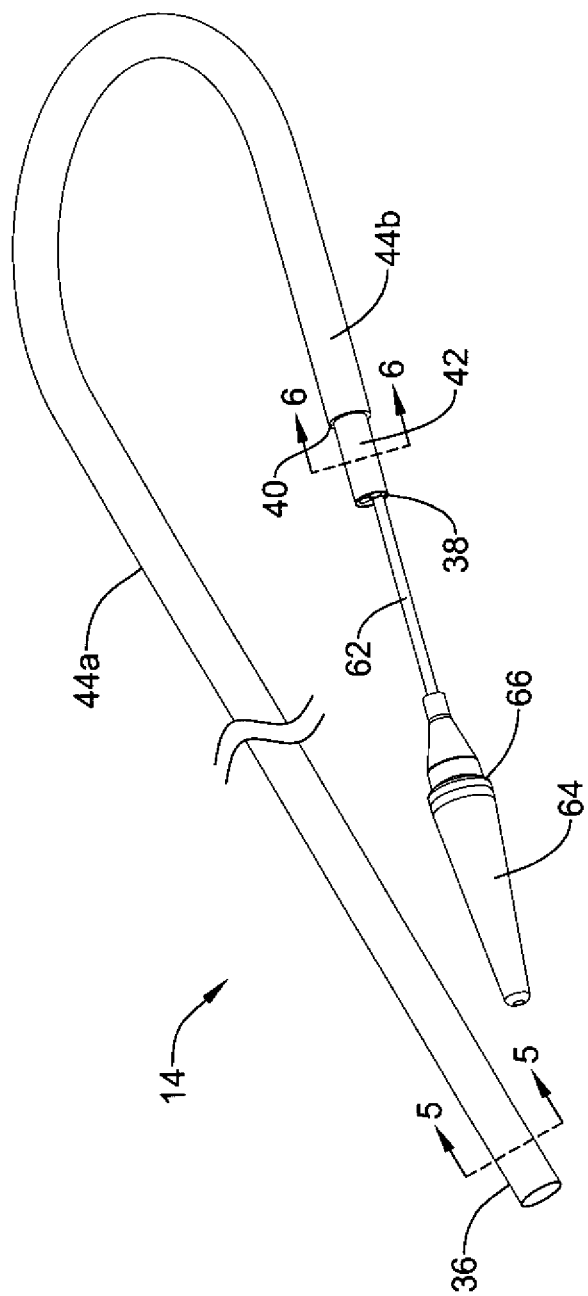
FIG. 4 is a side view of an example inner catheter.
Figure 5:
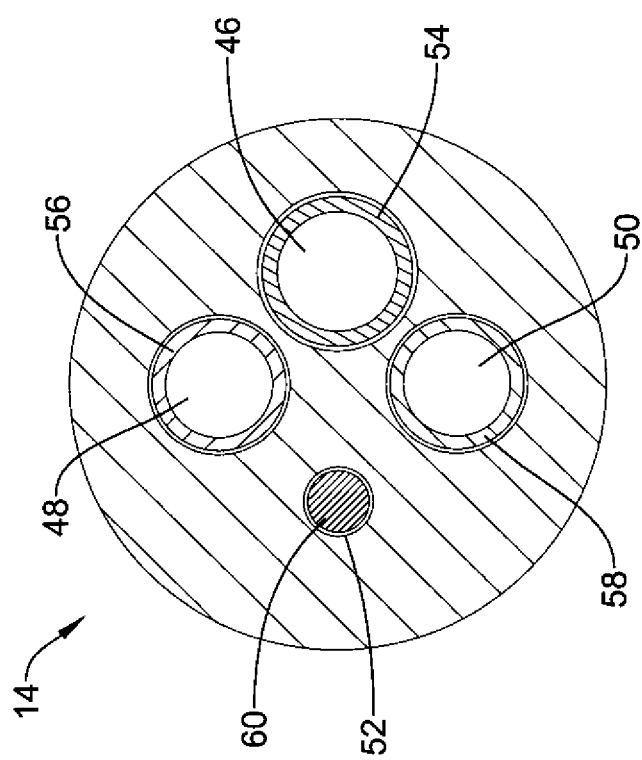
FIG. 5 is a cross-sectional view taken through line 5-5 in FIG. 4.

FIG. 4 is a side view of the inner catheter 14. A distal end region of inner catheter 14 may include a step in outer diameter 40 that defines a decreased outer diameter section 42. For example, decreased outer diameter section 42 may have an outer diameter in the range of about 0.127 to 0.635 cm (0.05 to 0.25 inches), or about 0.254 to 0.508 cm (0.10 to 0.20 inches), or about 0.38608±0.00762 (0.152±0.003 inches) as opposed to the remainder of inner catheter 14 where the outer diameter may be in the range of about 0.127 to 0.762 cm (0.05 to 0.30 inches), or about 0.254 to 0.635 cm (0.10 to 0.25 inches), or about 0.508±0.0254 cm (0.20±0.01 inches). Decreased outer diameter section 42 may define a region where other components of system 10 may be attached. Some additional details regarding these components can be found herein.

In general, inner catheter 14 may take the form of an extruded polymer tube. Other forms are also contemplated including other polymer tubes, metallic tubes, reinforced tubes, or the like including other suitable materials such as those disclosed herein. In some embodiments, inner catheter 14 is a singular monolithic or unitary member. In other embodiments, inner catheter 14 may include a plurality of portions or segments that are coupled together. The total length of inner catheter may be in the range of about 60 to 150 cm, or about 80 to 120 cm, or about 100 to 115 cm, or about 112±0.02 cm. Just like outer sheath 12, inner catheter 14 may also be curved, for example adjacent to the distal end thereof. In some embodiments, inner catheter 14 may have one or more sections with a differing hardness/stiffness (e.g., differing shore durometer). For example, inner catheter may have a proximal region 44a and an intermediate region 44b. Proximal region 44a may include a generally stiff polymeric material such as a 72D polyether block amide (e.g., 72D PEBAX) and may have a length in the range of about 60 to 150 cm, or about 80 to 120 cm, or about 100 to 115 cm, or about 109.5±0.02 cm. Intermediate region 44b may include a 40D polyether block amide (e.g., 40D PEBAX) and may have a length in the range of about 5 to 25 mm, or about 10 to 20 mm, or about 15±0.01 mm. Decreased outer diameter section 42 may also differ from regions 44a/44b and, in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples.

Figure 6:
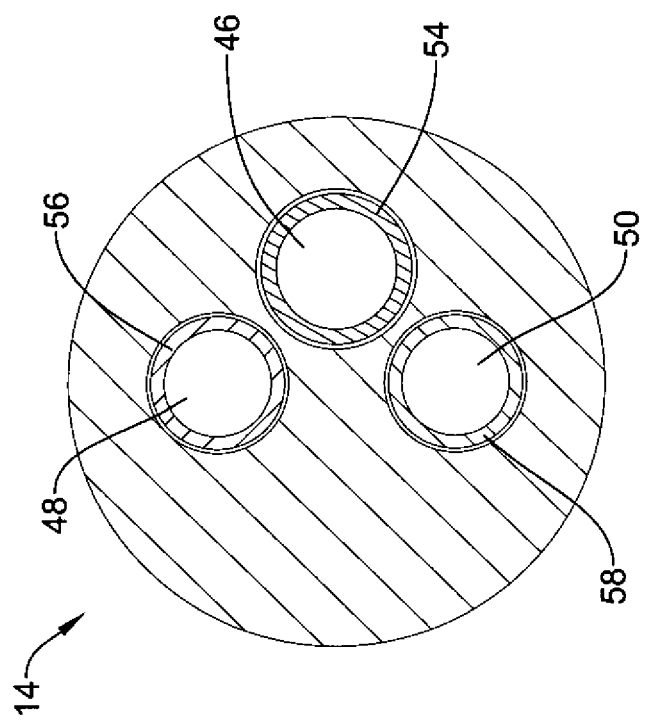
FIG. 6 is a cross-sectional view taken through line 6-6 in FIG. 4.

Inner catheter 14 may include one or more lumens. For example, FIG. 5 (which is a cross-sectional view of inner catheter 14 adjacent to proximal end portion 36) illustrates that inner catheter 14 may include a first lumen 46, a second lumen 48, a third lumen 50, and a fourth lumen 52. In general, lumens 46/48/50/52 extend along the entire length of inner catheter 14. Other embodiments are contemplated, however, where one or more of lumens 46/48/50/52 extend along only a portion of the length of inner catheter 14. For example, fourth lumen 52 may stop just short of the distal end of inner catheter 14 and/or be filled in at its distal end to effectively end fourth lumen 52 proximal of the distal end of inner catheter 14, as illustrated in FIG. 6 by the absence of fourth lumen 52 adjacent to the distal end of inner catheter 14.

Disposed within first lumen 46 may be push-pull rods 84 (not shown in FIG. 5, seen in other figures including FIG. 7), which are used to expand and/or elongate implant 16 as explained in more detail herein. In at least some embodiments, first lumen 46 may be lined with a low friction liner 54 (e.g., a FEP liner). Disposed within second lumen 48 may be a pin release mandrel 92 (not shown in FIG. 5, seen in other figures including FIG. 7), which is also explained in more detail herein. In at least some embodiments, second lumen 48 may be lined with a hypotube liner 56. Third lumen 50 may be a guidewire lumen and this lumen may also be lined with a hypotube liner 58.

Fourth lumen 52 may be used to house a non-stretch wire 60. The form of non-stretch wire 60 may vary. In some embodiments, non-stretch wire 60 may take the form of a stainless steel braid. The non-stretch wire 60 may optionally include a pair of longitudinally-extending aramid and/or para aramid strands (for example, KEVLAR®) disposed on opposite sides of the braid. In general, rather than being "disposed within" fourth lumen 52, non-stretch wire 60 may be embedded within fourth lumen 52. In addition, non-stretch wire 60 may extend to a position adjacent to distal end portion 38 but not fully to the distal end of inner catheter 14 as illustrated in FIG. 6 by the absence of fourth lumen 52 adjacent to the distal end of inner catheter 14. For example, a short distal segment of fourth lumen 52 may be filled in with polymer material adjacent to the distal end of inner catheter 14.

Inner catheter 14 may also include a guidewire extension tube 62 that extends distally from distal end portion 38. A nose cone 64 is attached to guidewire extension tube 62. Nose cone 64 generally is designed to have an atraumatic shape. Nose cone 64 may also include a ridge or ledge 66 that is configured to abut the distal tip 24 of outer sheath 12 during delivery of implant 16.

Figure 7:
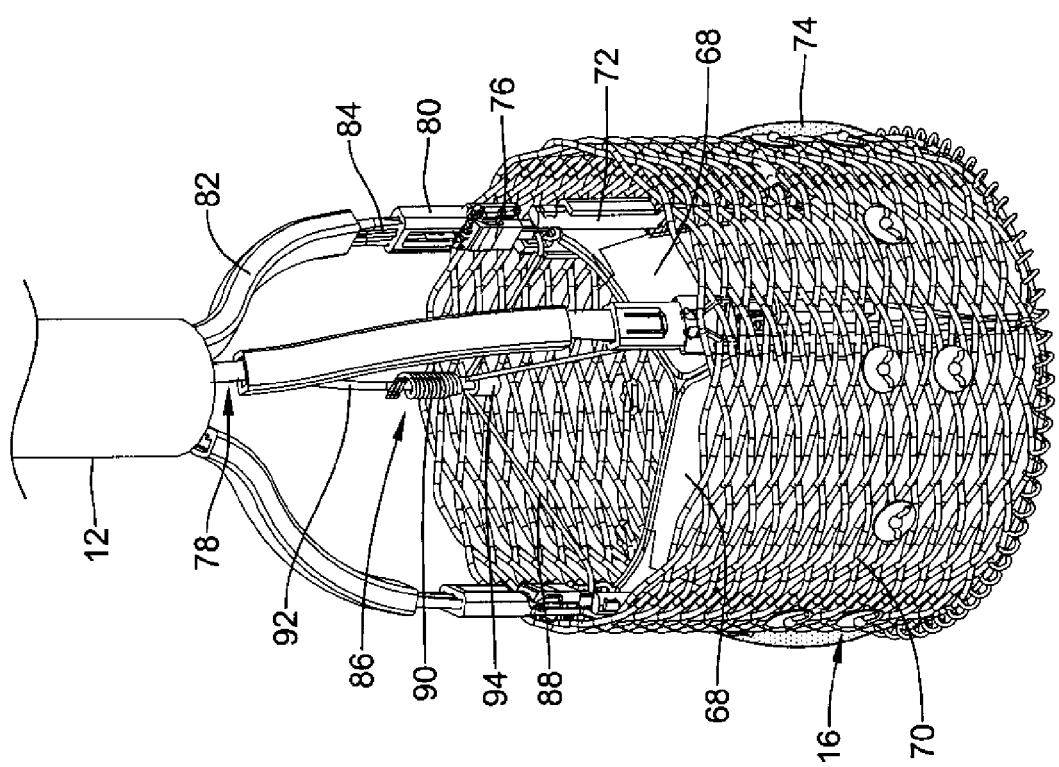
FIG. 7 is a perspective view of a portion of an example implant associated with the example medical device system.

FIG. 7 illustrates some of the additional components of system 10 and implant 16. For example, here it can be seen that implant 16 includes a plurality of valve leaflets 68 (e.g., bovine pericardial) which are secured to a cylindrical braid 70 at a post or commissure post 72, for example at the commissure portions of the leaflets 68. In this example, implant 16 includes three leaflets 68 secured to braid 70 with three posts 72. Leaflets 68 may also be secured to the base or "distal end" of braid 70. The posts 72, in turn, may be secured to braid 70 (e.g., along the interior of braid 70) with sutures or other suitable mechanisms. Positioned adjacent to (e.g., longitudinally spaced from and aligned with) posts 72 are a plurality of buckles 76, which may also be sutured to braid 70 (e.g., along the interior of braid 70). In this example, one buckle 76 is attached to braid 70 adjacent to each of the three posts 72. Accordingly, braid 70 has a total of three buckles 76 and three posts 72 attached thereto. Other embodiments are contemplated where fewer or more buckles 76 and posts 72 may be utilized. A seal 74 (shown in cross-section) may be disposed about braid 70 and, as the name suggests, may help to seal implant 16 within a target implant site or area of interest.

Attachment between implant 16 and inner catheter 14 (and/or outer sheath 12) may be effected through the use of a three finger coupler 78. Coupler 78 may generally include a cylindrical base (not shown) that is attached to inner catheter 14 (e.g., disposed about and attached to reduced outer diameter section 42). Projecting distally from the base are three fingers that are each configured to engage with implant 16 at posts 72 and buckles 76. A collar 80 may further assist in holding together these structures. A guide 82 may be disposed over each of the fingers and may serve to keep the fingers of coupler 78 associated with push-pull rods 84 extending adjacent to coupler 78. Finally, a pin release assembly 86 may be a linking structure that keeps posts 72, buckles 76, and push-pull rods 84 associated with one another. Pin release assembly 86 includes a plurality of individual pins 88 that may be joined together via a coiled connection 90 and held to a pin release mandrel 92 with a ferrule 94.

During delivery, implant 16 is secured at the distal end of inner catheter 14 by virtue of the association of the fingers of coupler 78 being coupled with a projecting proximal end of buckles 76 (and being held in place with collar 80 disposed over the connection) and by virtue of pins 88 securing together push-pull rods 84 and posts 72. When implant 16 is advanced within the anatomy to the desired location, outer sheath 12 may be withdrawn (e.g., moved proximally relative to inner catheter 14) to expose implant 16. Then, push-pull rods 84 can be used to expand and "lock" implant 16 in the expanded or deployed configuration by proximally retracting push-pull rods 84 to pull posts 72 into engagement with buckles 76. Finally, pins 88 can be removed, thereby uncoupling push-pull rods 84 from posts 72, which allows implant 16 to be released from system 10 and deployed in the anatomy.

Figure 8:
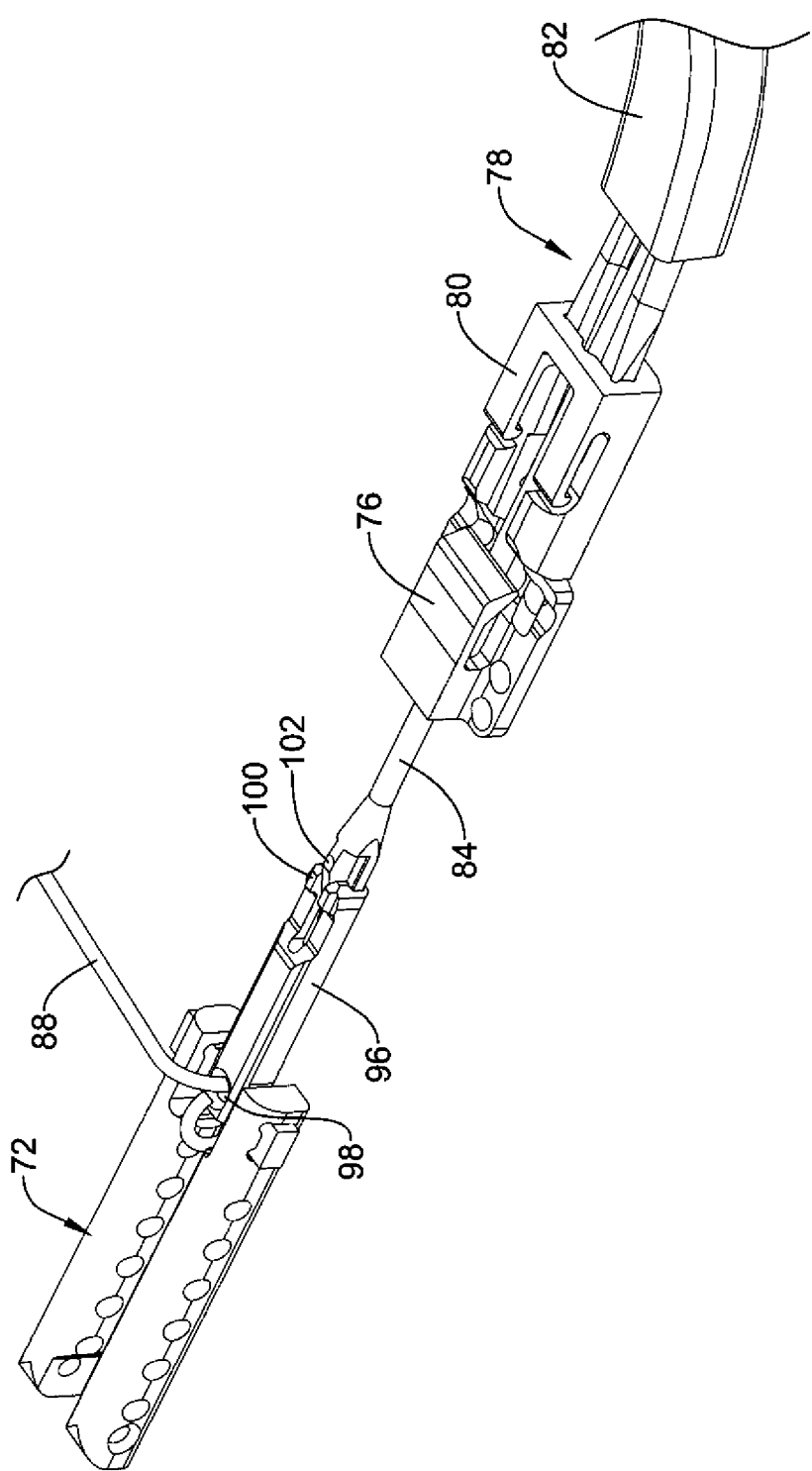
FIGS. 8-11 are perspective views that illustrate an example mechanism for locking an implant.

FIGS. 8-11 illustrate the locking system utilized with system 10. For simplicity purposes, only one of the three fingers of the coupler 78, only one of the three push-pull rods 84, and only one of the posts 72 of the example system 10 are shown (and implant 16 is not shown). As seen in FIG. 8, push-pull rod 84 extends through guide 82 adjacent to the fingers of coupler 78, through collar 80, through buckle 76, and into a hollow t-shaped bar portion 96 of post 72. The distal end of push-pull rod 84 may include an opening or aperture (not shown) that can be aligned with an opening 98 of t-shaped bar portion 96. When so aligned, pin 88 can be looped through opening 98 and the opening of push-pull rod 84. This secures push-pull rod 84 to post 72 and forms a configuration of these structures that can be utilized during delivery of implant 16. As can be appreciated, the proximal end of post 72 and the distal end of buckle 76 are longitudinally separated and, accordingly, implant 16 is in an elongated and generally low-profile configuration suitable for delivery.

Figure 9:
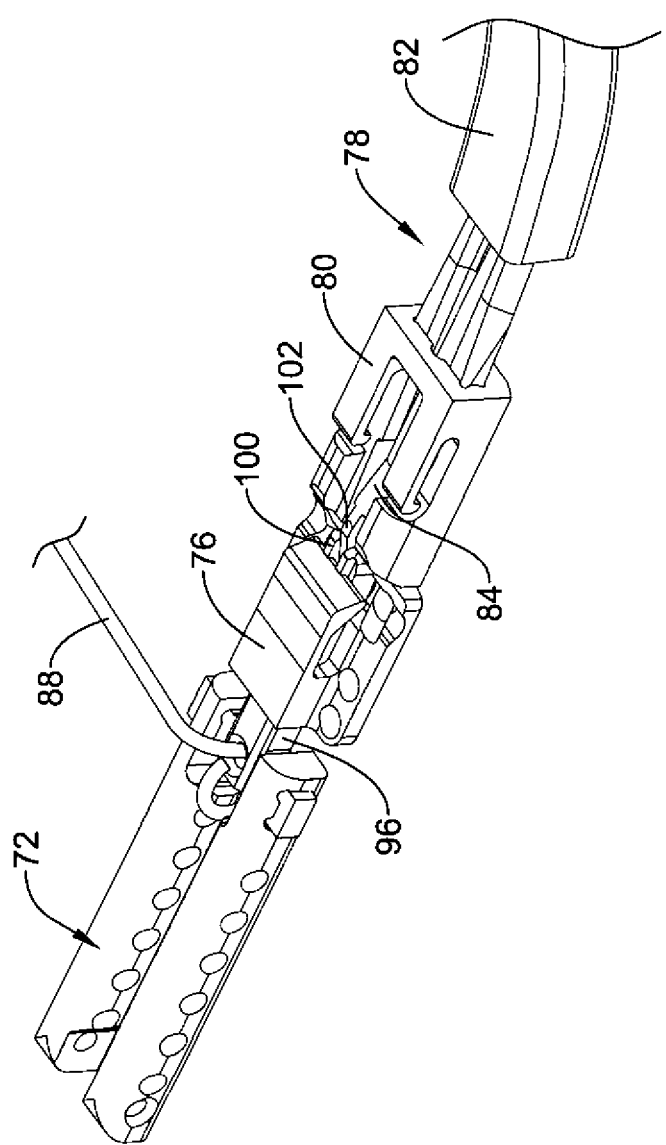
Figure 10:
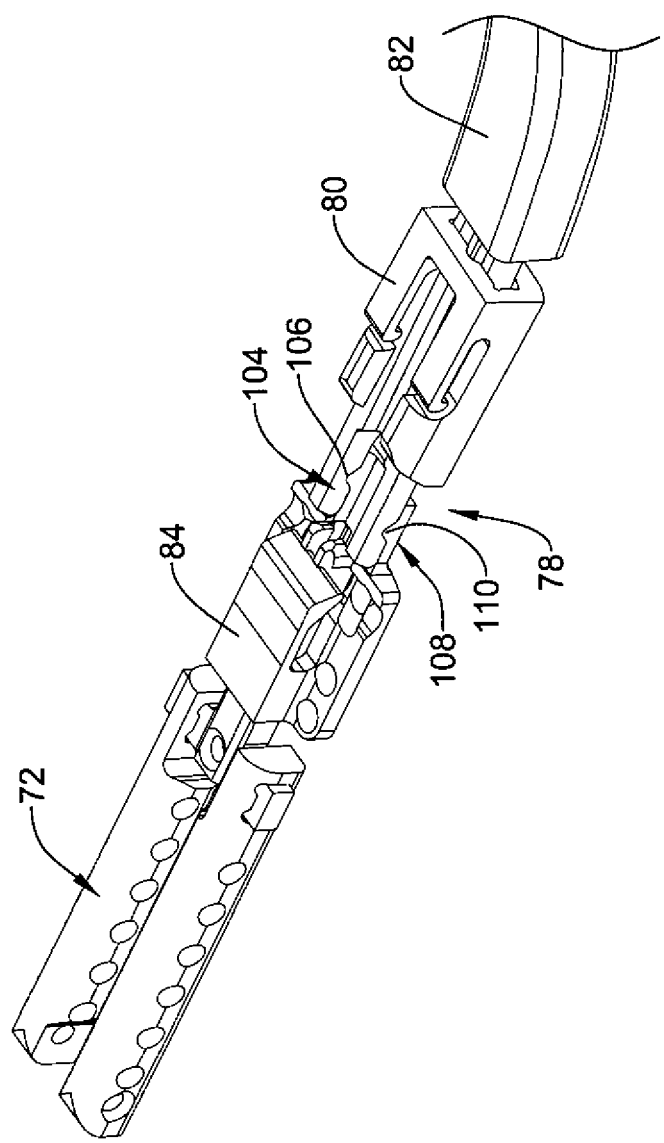
Figure 11:
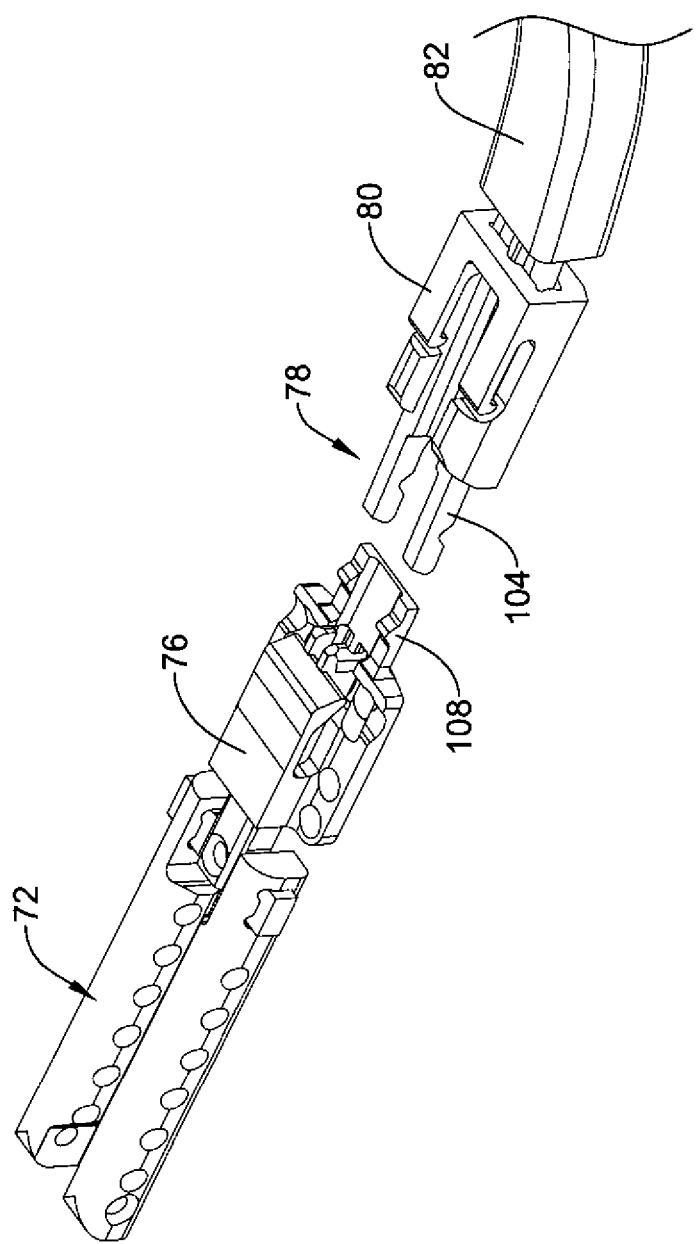

When implant 16 reaches the intended target site within the anatomy, a clinician can proximally retract push-pull rod 84, thereby moving the proximal ends of posts 72 toward the distal ends of buckles 76 in order to expand implant 16. Ultimately, push-pull rod 84 can be retracted sufficiently far enough to lock post 72 with buckle 76 so as to lock implant in an expanded configuration suitable for implantation within the anatomy. FIG. 9 illustrates push-pull rod 84 proximally retracted. In doing so, post 72 is brought into contact with buckle 76. More particularly, a raised, generally transversely-oriented ridge 100 on t-shaped bar portion 96 may be pulled proximally past buckle 76 so that post 72 is secured and held in place by buckle 76. At this point, it is possible to urge push-pull rods 84 distally to "unlock" implant 16, thereby allowing for repositioning and/or retraction. Alternatively, if a clinician is satisfied with the positioning and/or locking of implant 16 (e.g., after visualization of implant 16 via a suitable imaging technique), pins 88 may be pulled (e.g., removed from openings 98 and the openings in push-pull rods 84) to uncouple push-pull rods 84 from posts 72 as shown in FIG. 10. Further retraction of push-pull rods 84 causes a longitudinally-oriented ridge 102 on push-pull rods 84 to engage collar 80 and causes collar 80 to slide proximally along the fingers of coupler 78. In doing so, a forked end 104 of the fingers, which has a groove 106 formed therein, is exposed and can be uncoupled from a rail 108, which has a projection 110 formed thereon that is configured to mate with groove 106, as shown in FIG. 11. Thereafter, system 10 can be removed from the anatomy, leaving behind the expanded and deployed implant 16.

Figure 12:
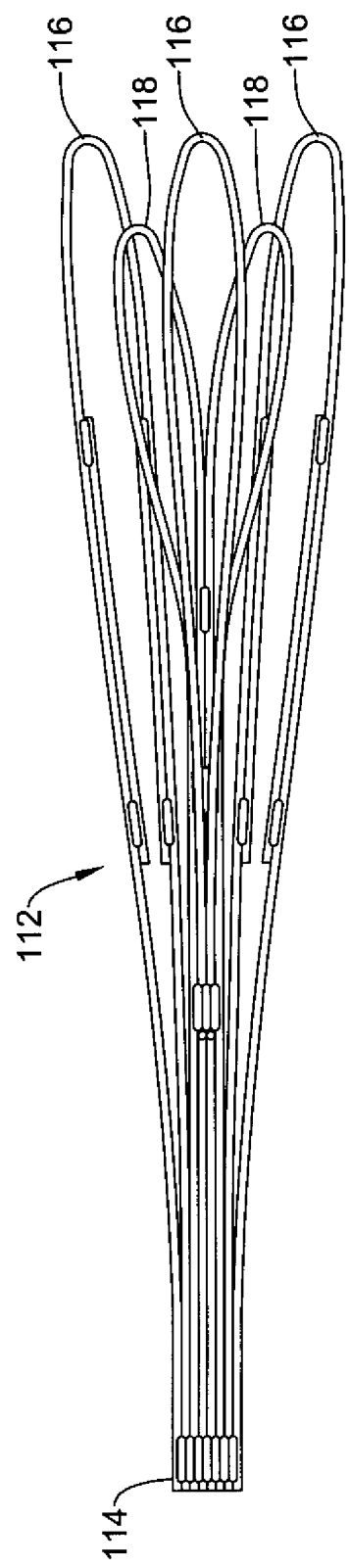
FIG. 12 is a side view of a portion of an example sheathing aid.
Figure 13:
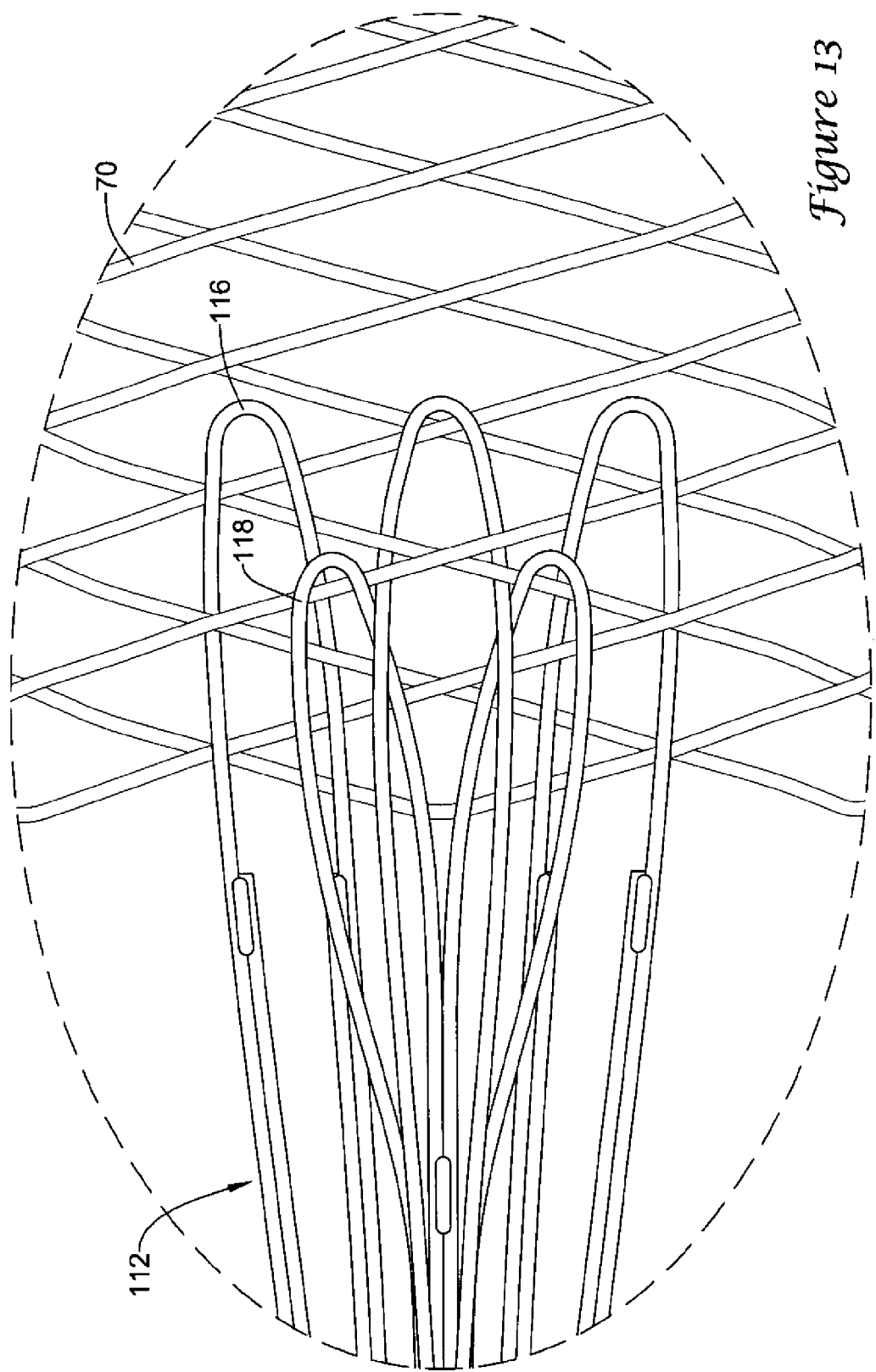
FIG. 13 is an enlarged plan view illustrating engagement of the example sheathing aid with an example implant.

FIGS. 12-13 illustrate another component that may be included with system 10. For example, FIG. 12 is a side view of a portion of a sheathing aid 112. Here it can be seen that sheathing aid 112 includes a base 114 and a group of petals including a set of three longer petals 116 and a pair of shorter petals 118. In use, a group of petals 116/118 may be positioned between each of the fingers of coupler 78. Because the coupler 78 may have a total of three fingers, sheathing aid 112 may have a total of fifteen petals (e.g., three groups that each include three "long" petals 116 and two "short" petals 118, with each group being positioned between adjacent pairs of fingers of coupler 78). Base 114 may be secured to inner catheter 14 adjacent to coupler 78 (e.g., underneath coupler 78 and between coupler 78 and inner catheter 14).

Sheathing aid 112, as the name suggests, may be used to aid in the sheathing of implant 16 into outer sheath 12. In addition, sheathing aid 112 may aid in the initial sheathing of implant 16 (e.g., removing implant 16 from a packaging container such as a bottle and pulling implant 16 into outer sheath 12) and in re-sheathing implant 16 during repositioning and/or retraction of implant 16 within the area of interest. Sheathing may be accomplished via the arrangement and positioning of the various petals 116/118. For example, FIG. 13 illustrates the longer petals 116 woven in and out of braid 70, and the shorter petals 118 disposed along the exterior of braid 70 acting as a funnel for sheathing.

Figure 14:
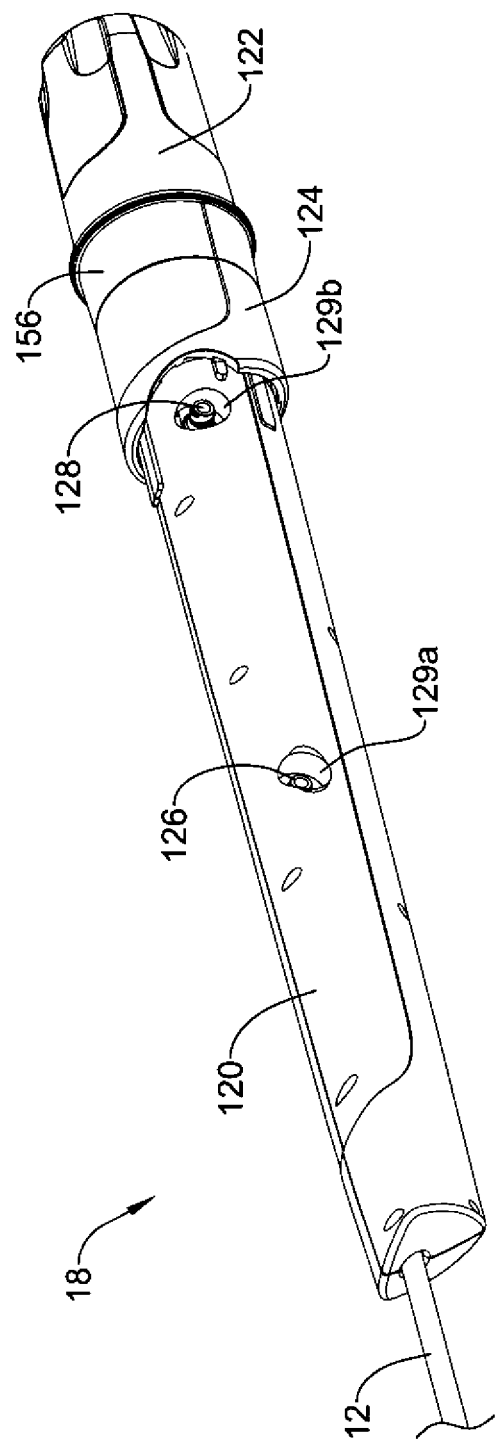
FIG. 14 is a side view of an example handle.

FIG. 14 is a side view of handle 18. Here it can be seen that handle 18 includes a handle housing 120. A rotatable control knob 122 may be disposed about handle housing 120 (e.g., at a proximal end of handle housing 120) and may be used to move one or more of the components of system 10 (e.g., outer sheath 12, push-pull rods 84, etc.). A rotatable collar 156 may be disposed about the handle housing 120. In some embodiments, control knob 122 may be disposed about a proximal portion of collar 156. A slidable door 124 may also be disposed about handle housing 120. Door 124 may translate distally to expose a distal portion of rotatable collar 156 (not shown in FIG. 14, can be seen in other figures including FIGS. 19-20) positioned generally under door 124. Collar 156 may be rotated to move one or more components of system 10 (e.g., push-pull rods 84, pin release mandrel 92, etc.). Some additional details related to exterior elements of handle 18 (e.g., door 124, collar 156, etc.) may be seen in FIGS. 23-25A and are discussed further herein.

Handle 18 may also include one or more apertures 129a/129b and/or flush ports 126/128 that can be used to flush system 10. In some embodiments, distal flush port 126 and proximal flush port 128 may be accessible from the exterior of the handle housing 120 through distal aperture 129a and proximal aperture 129b, respectively.

Figure 15:
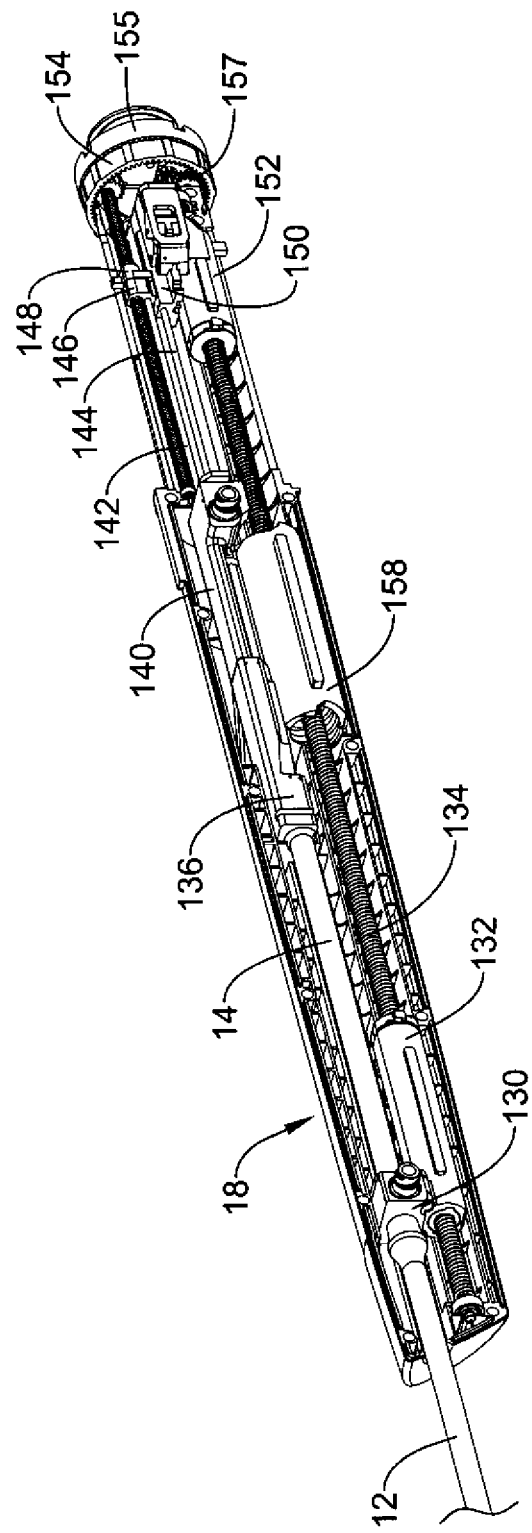
FIG. 15 is a cut away view illustrating some of the interior components of the example handle.

FIG. 15 is a side view of handle 18 with a portion of handle housing 120 removed, exposing at least some of the interior components. Here it can be seen that outer sheath 12 may be attached to a sheath adapter 130. Sheath adapter 130 is attached to a sheath carriage 132, which may be threaded onto a lead screw 134. Distal flush port 126 may be disposed on sheath adapter 130. In general, distal flush port 126 provides access to the interior or lumen of outer sheath 12 (e.g., access to space between inner catheter 14 and outer sheath 12) so that a clinician can flush fluid through the lumen of outer sheath 12 to remove any unwanted materials (e.g., air, fluid, contaminants, etc.) therein prior to use of system 10. In at least some embodiments, distal flush port 126 has a luer type connector (e.g., a one-way luer connector) that allows a device such as a syringe with a corresponding connector to be attached thereto for flushing.

Extending through and proximally from sheath adapter 130 is inner catheter 14. A proximal end of inner catheter 14 is attached (e.g., fixedly attached) to an interior body or diverter 136. Diverter 136 is attached to a support body 140. In general, diverter 136 and/or support body 140 may have one or more passageways or lumens formed therein. In some embodiments, push-pull rods 84 and/or pin release mandrel 92 may extend through respective passageways. Alternatively, the proximal ends of push-pull rods 84 and/or pin release mandrel 92 may each be attached to a shaft or hypotube (e.g., solid in cross-section, tubular, etc.), and each of the shafts may extend through the one or more passageways. For example, a first shaft or hypotube 142 and a second shaft or hypotube 144 may extend through the passageways in diverter 136, and in some embodiments, the first shaft or hypotube 142 extends through a first passageway and the second shaft or hypotube 144 extends through a second passageway that is separate or distinct from the first passageway. In at least some embodiments, first shaft 142 is attached to pin release mandrel 92. In at least some embodiments, second shaft 144 is attached to push-pull rods 84. It should be noted that at in least some embodiments of system 10, three push-pull rods 84 are utilized. In these embodiments, the three push-pull rods 84 come together (e.g., brought into contact with one another or otherwise brought into relatively close proximity with one another) adjacent to the distal end of inner catheter 14 and enter first lumen 46. At one or more positions along their length, push-pull rods 84 may be attached to one another. For example, in some embodiments, push-pull rods 84 may be welded together about 10.16 cm (about 4.00 inches) from their distal ends. In some embodiments, push-pull rods 84 may be welded together proximate their proximal ends in addition to or instead of the distal weld. Proximally thereafter, push-pull rods 84 may extend to second shaft 144.

A hypotube (e.g., hypotube liner 58 disposed along guidewire lumen 52) may extend through diverter 136 within a passageway therein and then be "diverted" around a portion of diverter 136 and support body 140, and ultimately be extended to a position at the proximal end of handle 18 so as to provide a user access to guidewire lumen 52. Proximal flush port 128 may be disposed on support body 140 that can be used to flush the lumens of inner catheter 14 and, for example, may function similarly to distal flush port 126.

At their respective proximal ends, first shaft 142 may be secured to a slider 146 and second shaft 144 may be secured to a force limiter body 150. The connections between the various components may include a number of different types of connections including mechanical bonding (e.g., pinning, threading, interference fit, etc.), adhesive bonding, thermal bonding, etc. Slider 146 may be slidable relative to force limiter body 150. In some embodiments, slider 146 may be selectively locked to force limiter body 150, thereby preventing relative movement between the slider 146 and the force limiter body 150. Force limiter body 150 may be secured to a push-pull rod carriage 152, which may be threaded onto lead screw 134. Thus, movement of lead screw 134 can cause movement of push-pull rod carriage 152 and force limiter body 150 and thus, push-pull rods 84 (via second shaft 144). Some additional details regarding this motion can be found herein.

In general, force limiter body 150 forms or defines a stop point that provides tactile feedback (e.g., resistance to further rotation of control knob 122) to the user indicating that push-pull rods 84 have been retracted proximally a sufficient distance to lock posts 72 with buckles 76. To verify proper locking, a clinician may use an appropriate visualization technique to visualize proper locking (e.g., the relative positioning of the posts 72 and the buckles 76). A chock 148 may be positioned adjacent to slider 146 to selectively lock slider 146 to force limiter body 150. In order to allow pin release mandrel 92 to be proximally retracted to pull pins 88, chock 148 can be rotated or otherwise moved to a secondary position or configuration. When in this configuration, chock 148 no longer forms a barrier to further movement of, for example, slider 146 and pin release mandrel 92. Accordingly, with chock 148 no longer acting as an impediment, slider 146 and pin release mandrel 92 can be proximally retracted to facilitate deployment of implant 16 by allowing pins 88 to be pulled.

Handle 18 also includes a rotatable ring 155 with internal teeth that are configured to engage with teeth on a gear 157 coupled to lead screw 134. Ring 155 is coupled to control knob 122 so that rotation of control knob 122 results in analogous motion of ring 155 and thus lead screw 134.

Handle 18 is generally configured for coordinated movement of multiple structures of system 10. For example, handle 18 is configured to allow a user to move outer sheath 12 (e.g., relative to inner catheter 14), move push-pull rods 84, and move pin release mandrel 92. Moreover, handle 18 is configured so that the appropriate structure can be moved at the appropriate time during the intervention so that implant 16 can be delivered in an efficient manner. Some examples of how the coordinated movement of system 10 may occur within handle 18 may be similar to those disclosed in U.S. Patent Application Pub. No. US 2010/0280495, the entire disclosure of which is herein incorporated by reference.

Figure 16:
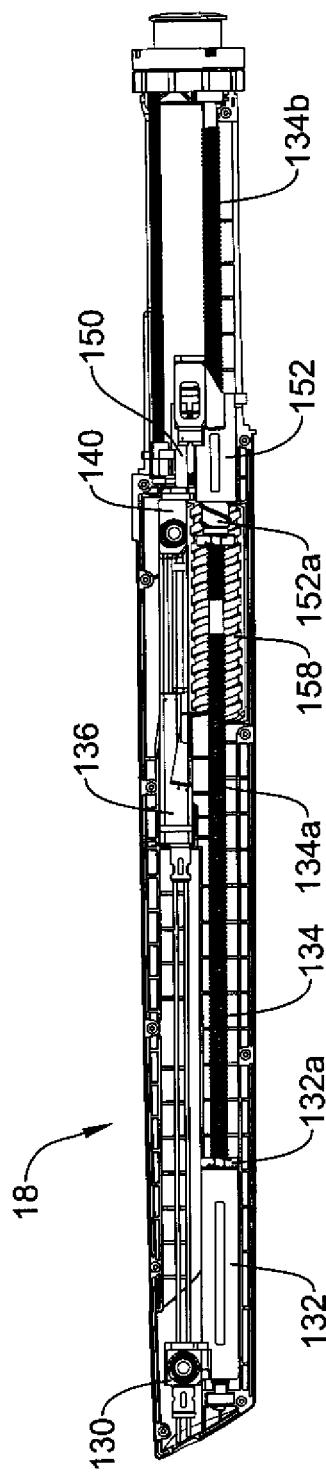
FIGS. 16-18 illustrate an example of coordinated movement of handle components within the example handle.

To help facilitate the coordinated movement, handle 18 may include a lost motion barrel 158. Lost motion barrel 158 is configured to engage carriages 132/152 and/or screws associated with carriages 132/152 at different times during the intervention to stop motion (e.g., create "lost motion" of the appropriate carriage). FIGS. 16-19 illustrate some of the coordinated motion achieved by handle 18. It should be noted that some elements of system 10 are not shown in FIGS. 16-20 for clarity. For example, FIG. 16 illustrates a first position or state for handle 18 where outer sheath 12 is extended distally relative to inner catheter 14 (and handle 18) so as to fully sheath (e.g., contain) implant 16. While in this position, sheath carriage 132 is positioned adjacent to the distal end of handle 18. In addition, a rod screw 152*a* associated with push-pull rod carriage 152 is extended distally from push-pull rod carriage 152 and positioned within lost motion barrel 158. Upon rotation of control knob 122 (e.g., in the clockwise direction), lead screw 134 begins to rotate. Rotation of lead screw 134 causes sheath carriage 132 to move along lead screw 134 in the proximal direction, resulting in proximal movement of outer sheath 12 (e.g., "unsheathing" implant 16). This initial rotation of lead screw 134 also causes rod screw 152*a* to rotate. This may be because, for example, a knob or projection (not shown) on rod screw 152*a* may be engaged with a helical thread disposed along the interior of lost motion barrel 158. However, because rod screw 152*a* is spaced from push-pull rod carriage 152, it does not exert a force onto push-pull rod carriage 152. Thus, initial motion of control knob 122 does not result in movement of push-pull rod carriage 152 and, instead, only results in translation of sheath carriage 132 and rotation (and translation) of rod screw 152*a*.

Figure 17:
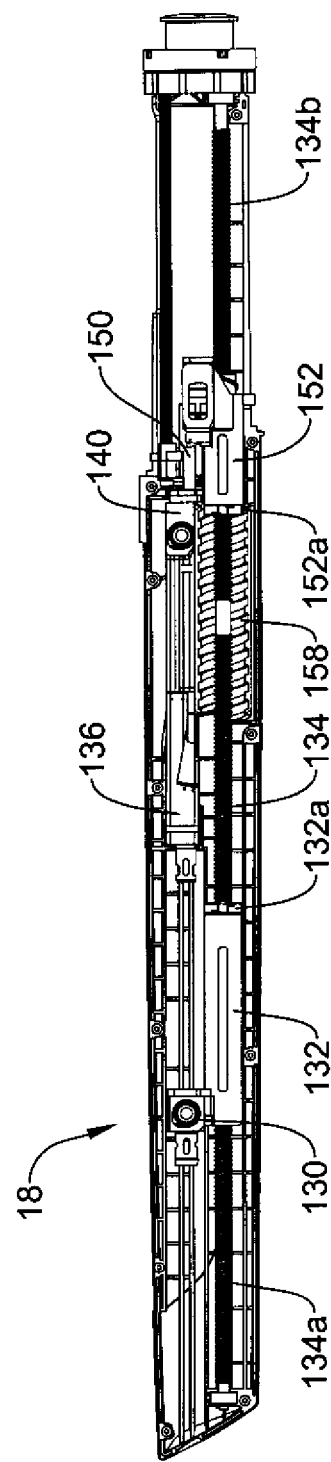

Eventually, rod screw 152*a* (e.g., the knob formed therein) reaches an essentially linear thread or pathway formed at the end of lost motion barrel 158. The linear thread allows rod screw 152*a* to translate along lead screw 134 to a position where rod screw 152*a* contacts (e.g., is threaded within and abuts) push-pull rod carriage 152. In doing so, rod screw 152*a* can contact and move proximally push-pull carriage 152. Accordingly, further rotation of lead screw 134 not only causes sheath carriage 132 to move proximally but also causes push-pull rod carriage 152 to move proximally as shown in FIG. 17.

Figure 18:
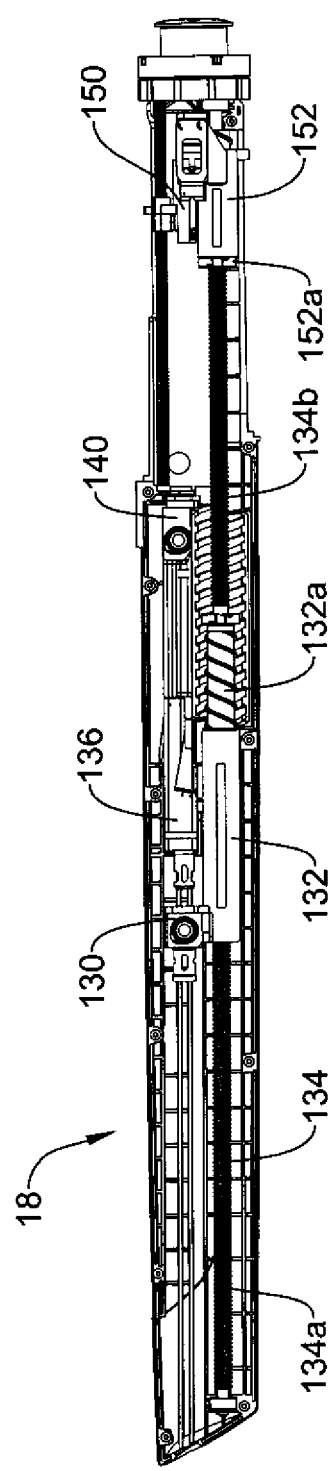

When sheath carriage 132 reaches lost motion barrel 158, a sheath carriage screw 132*a* of sheath carriage 132 enters lost motion barrel 158 as shown in FIG. 18. This may occur in a manner similar to how rod screw 152*a* threads and unthreads with the helical thread formed along lost motion barrel 158. For example, while sheath carriage 132 is translating, sheath carriage screw 132*a* may follow an essentially linear thread or pathway formed along or adjacent to lost motion barrel 158. Upon reaching lost motion barrel 158, sheath carriage screw 132*a* (e.g., a knob or projection formed thereon) may shift into engagement with the helical thread within lost motion barrel 158 and rotate. This rotation "unthreads" sheath carriage screw 132*a* from sheath carriage 132. Accordingly, additional rotation of lead screw 134 results in continued proximal movement of push-pull rod carriage 152 while motion of sheath carriage 132 ceases.

In at least some embodiments, lead screw 132 has a plurality of portions, for example a first portion 132*a* and a second portion 132*b*, with a differing pitch to its thread. This may allow carriages 132/152 to travel at different rates along lead screw 132. For example, the pitch of lead screw 132 along which sheath carriage 132 translates may be generally more spaced or slanted than at positions adjacent to push-pull rod carriage 152. Accordingly, the coordinated movement of carriages 132/152 also may be configured so that sheath carriage 132 translates along lead screw 132 at a greater rate than push-pull rod carriage 152. Other configurations are contemplated where the above-mentioned configuration is reversed as well as further configurations where the pitch of lead screw 132 is essentially constant or includes a number of different pitch regions.

Sufficient proximal retraction of push-pull rod carriage 152, for example as shown in FIG. 18, may result in push-pull rods 84 being sufficiently retracted so that posts 72 can engage and lock with buckles 76. When the clinician is satisfied that locking is complete (e.g., after verification via an appropriate visualization technique), the clinician may proximally retract pin release mandrel 92 in order to pull pins 88 from openings 98 and openings in push-pull rods 84 to release implant 16.

Figure 19:
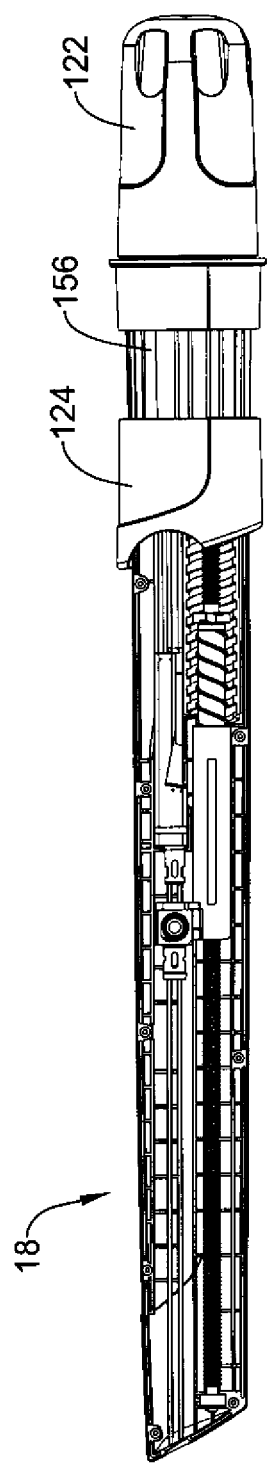
FIGS. 19-20 illustrate the rotation of a collar on the example handle.
Figure 20:
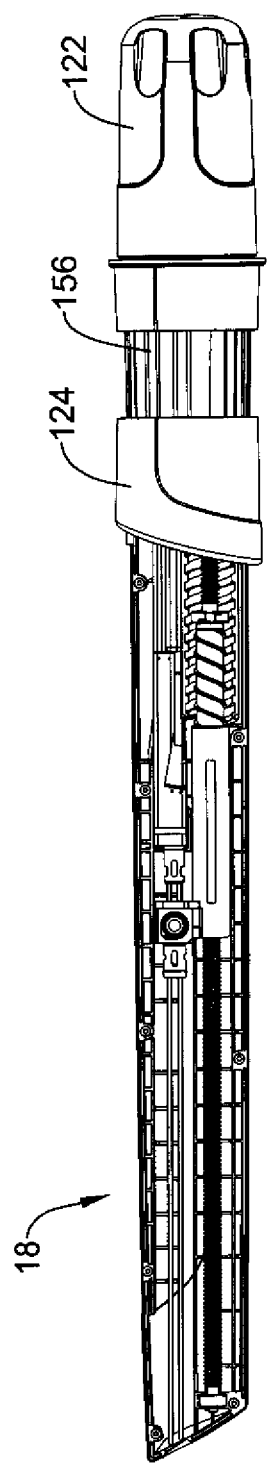

To initiate release of pins 88, door 124 may be slid distally along a collar 156 (which is positioned on handle 18) as shown in FIG. 19. When door 124 is sufficiently advanced, door 124 and collar 156, together, can be rotated as shown in FIG. 20. Push-pull rod carriage 152 may also include a radially-extending proximal flag member 164. In general, flag member 164 may be designed as a feature that can prevent collar 156 from being rotated earlier than desired (and, thus, prevent pins 88 from being pulled earlier than desired). For example, flag member 164 may be positioned within and follow a groove (not shown) along the interior of collar 156. While positioned within the groove, flag member 164 essentially forms a physical barrier that prevents collar 156 from rotating relative to handle housing 120. When push-pull rod carriage 152 is translated proximally to the back of handle housing 120 (e.g., when push-pull rods 84 are proximally retracted so as to lock posts 72 with buckles 76), flag member 164 exits the groove in collar 156. Accordingly, flag member 164 no longer impedes rotation of collar 156 and, as such, collar 156 can now be rotated to pull pins 88.

Figure 21:
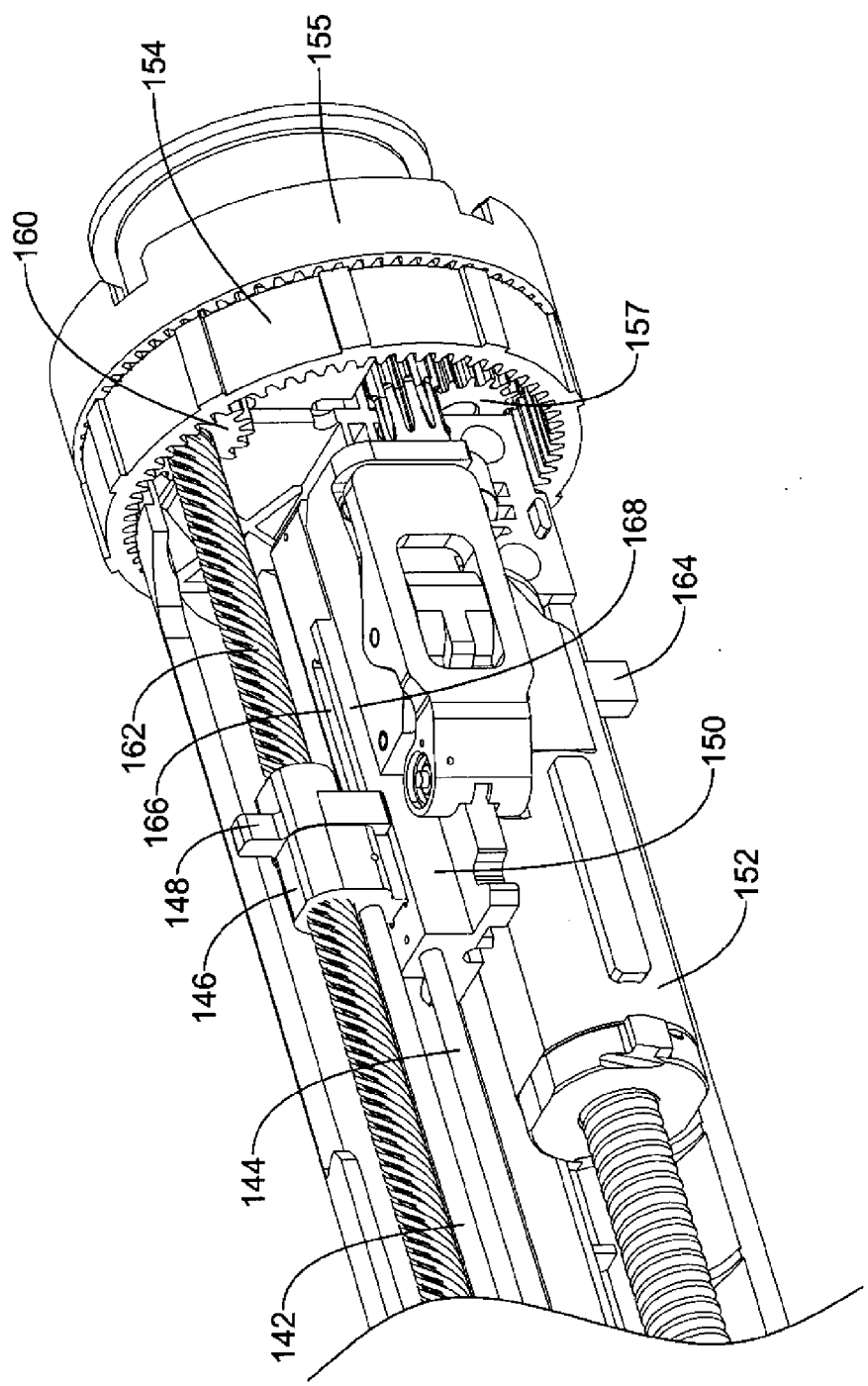
FIGS. 21-22 illustrate some of the components within the example handle during rotation of the collar.
Figure 22:
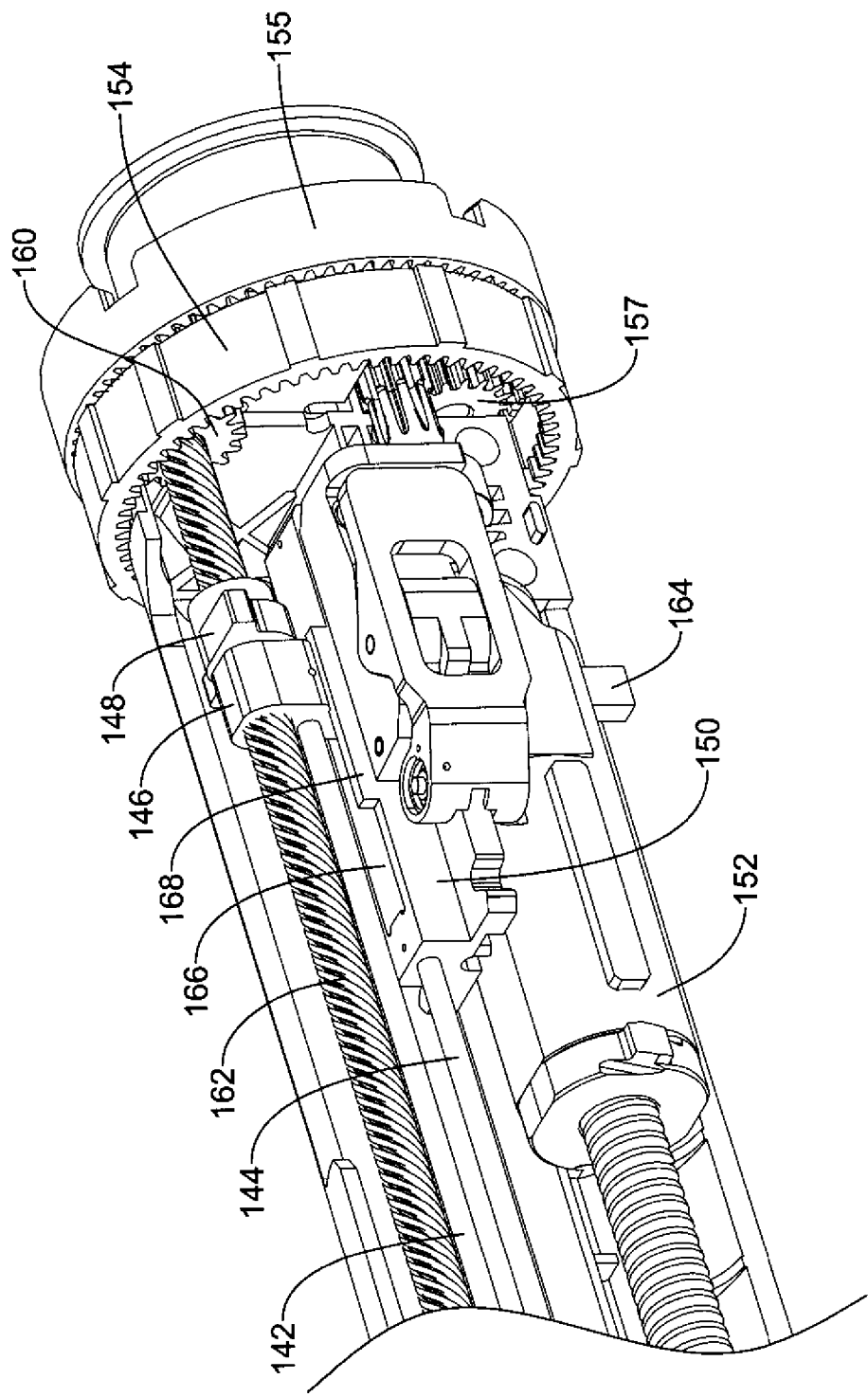

Collar 156, via ring 154, is associated with a gear 160 engaged with a secondary screw 162. Notches at a proximal end of collar 156 engage protrusions on ring 154 such that rotation of collar 156 causes corresponding rotation of ring 154 and thus secondary screw 162. The initial rotation of collar 156 is sufficient to rotate chock 148 (e.g., via a mechanical interaction between collar 156 and chock 148 that causes chock 148 to shift) from a first configuration where slider 146 (and, thus, pin release mandrel 92) is selectively locked to force limiter body 150, to a secondary configuration, which permits slider 146 to translate along secondary screw 162 as secondary screw 162 rotates, to proximally retract and pull pins 88 (e.g., via pin release mandrel 92). As seen in FIG. 21, chock 148 in the first configuration engages a ridge 168 along a top portion of force limiter body 150 which forms a physical barrier that prevents proximal translation of slider 146 relative to force limiter body 150. When collar 156 is rotated to shift chock 148 into the secondary configuration, slider 146 can translate proximally within a groove 166 disposed in the top portion of force limiter body 150 (e.g., as seen in FIG. 22), as collar 156 is rotated about the handle housing 120 to pull the pins 88 from the openings 98 and the openings in the distal ends of the push-pull rods 84. Once pins 88 have been removed, push-pull rods 84 may be withdrawn from implant 16, thereby deploying the implant at the target site (area of interest).

Following deployment of the implant 16, the control knob 122 may be rotated to move the sheath carriage 132 distally within the handle housing 120, thereby moving outer sheath 12 distally relative to inner catheter 14 and three-finger coupler 78 so as to cover or re-sheath the elements of system 10 disposed at the distal end. System 10 may then be removed from the patient's anatomy.

FIGS. 23-32A illustrate some elements of handle 18, and the movements of those elements that facilitate some functions of system 10. In certain figures, notably FIGS. 25, 27, 29, 31, and 32, some elements are shown in broken or hidden lines to improve clarity and to show the interaction or relationship between certain features that would otherwise be obscured from view.

Figure 23:
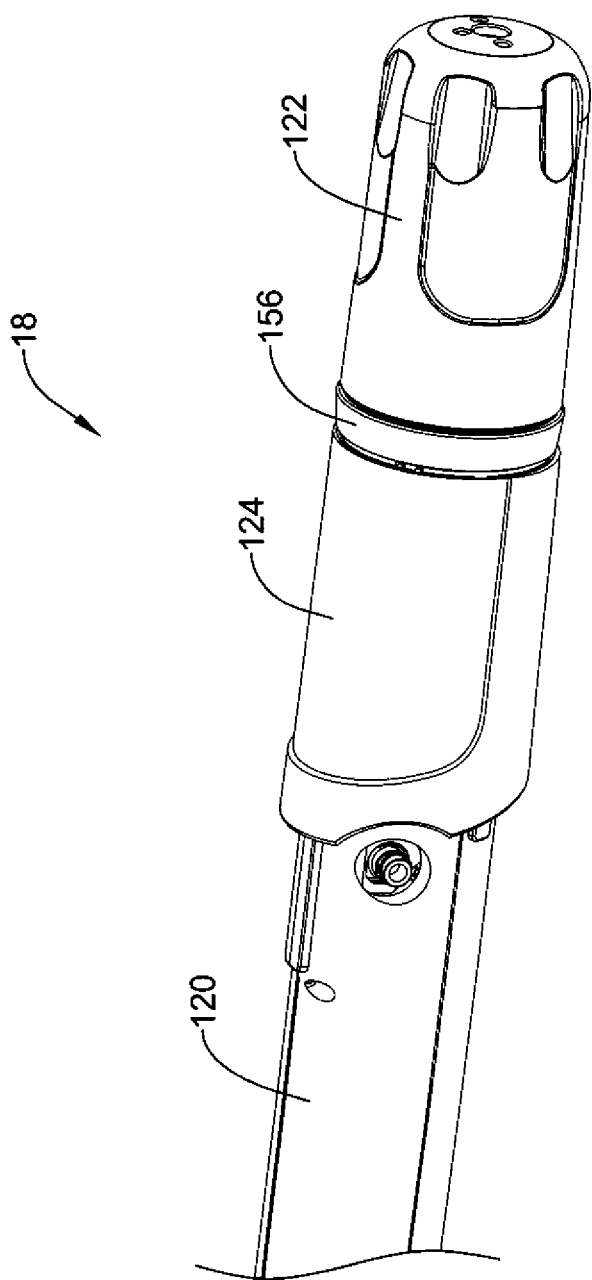
FIG. 23 illustrates some alternative elements of the example handle of FIGS. 14-22.

FIG. 23 generally shows a proximal end of handle 18. As discussed above, handle 18 may include a handle housing 120. A collar 156 may be disposed about the proximal end of handle housing 120. Control knob 122 may be disposed at the proximal end of handle housing 120, and in some embodiments, may be disposed about a proximal portion of collar 156. Control knob 122 is selectively rotatable about the longitudinal axis of handle housing 120 and/or the proximal portion of collar 156, and may function as described above. Slidable door 124, shown in greater detail in FIGS. 32-32A, may be disposed about handle housing 120 and/or a distal portion of collar 156.

Figure 24:
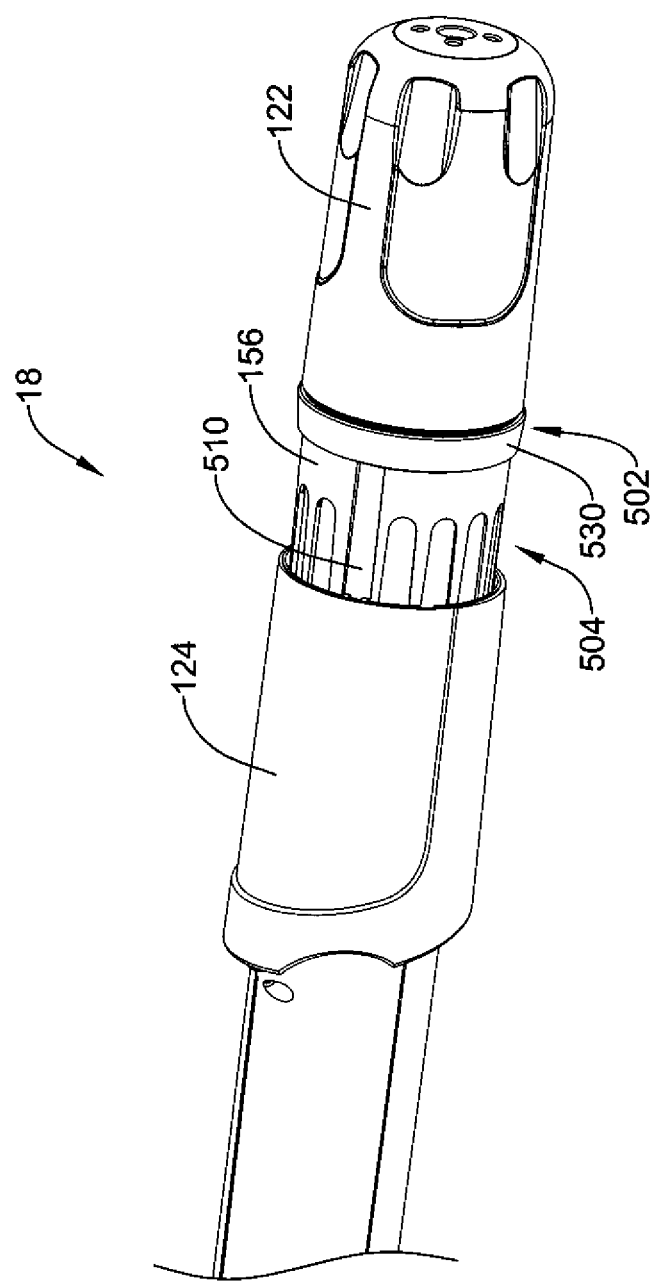
FIGS. 24-31 illustrate the movement of the door of FIG. 23 on the example handle.
Figure 25:
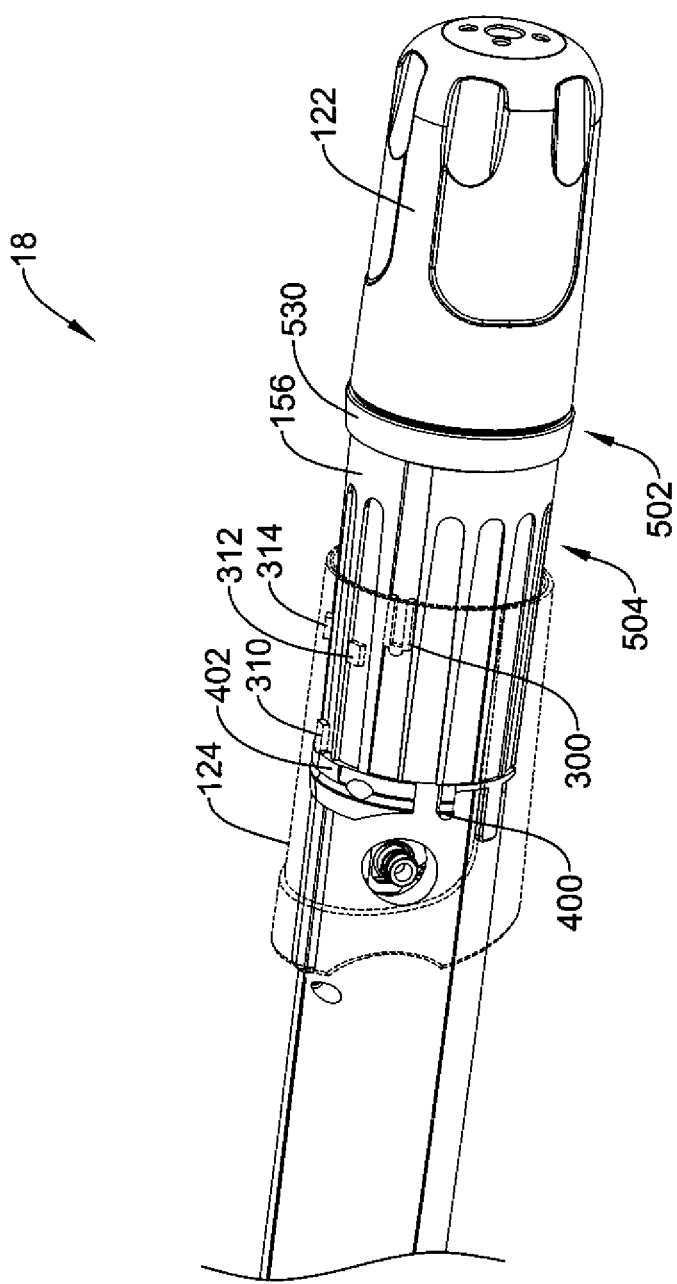

Collar 156 may be selectively rotatable about handle housing 120, as described above. Collar 156 may include a proximal portion (not shown), a central portion 502, and a distal portion 504, as illustrated in FIG. 25. The proximal portion may include a plurality of notches (not shown) configured to engage a plurality of protrusions on ring 154, as described above. Central portion 502 may include a radially-extending transverse flange portion 530 disposed about the central portion 502. As may be seen in FIG. 23, flange portion 530 may longitudinally space control knob 122 apart from door 124. Collar 156 may further include a longitudinally-oriented groove (not shown) on the interior of collar 156. Radially-extending flag member 164 of push-pull rod carriage 152 may be positioned within the groove to act as an interlocking element in an engaged configuration. In the engaged configuration, where flag member 164 is positioned within the groove, the flag member physically prevents collar 156 from rotating relative to handle housing 120. As push-pull rod carriage 152 is translated proximally within handle housing 120, the flag member 164 similarly translates proximally within the groove. When push-pull rod carriage 152 has translated proximally a sufficient distance, flag member 164 exits the groove to achieve a disengaged configuration. In the disengaged configuration, collar 156 is permitted to rotate relative to handle housing 120. Distal portion 504 may include a plurality of longitudinally-oriented recessed slots 510 in an outer surface thereof, as seen in FIGS. 24-31.

Figure 28:
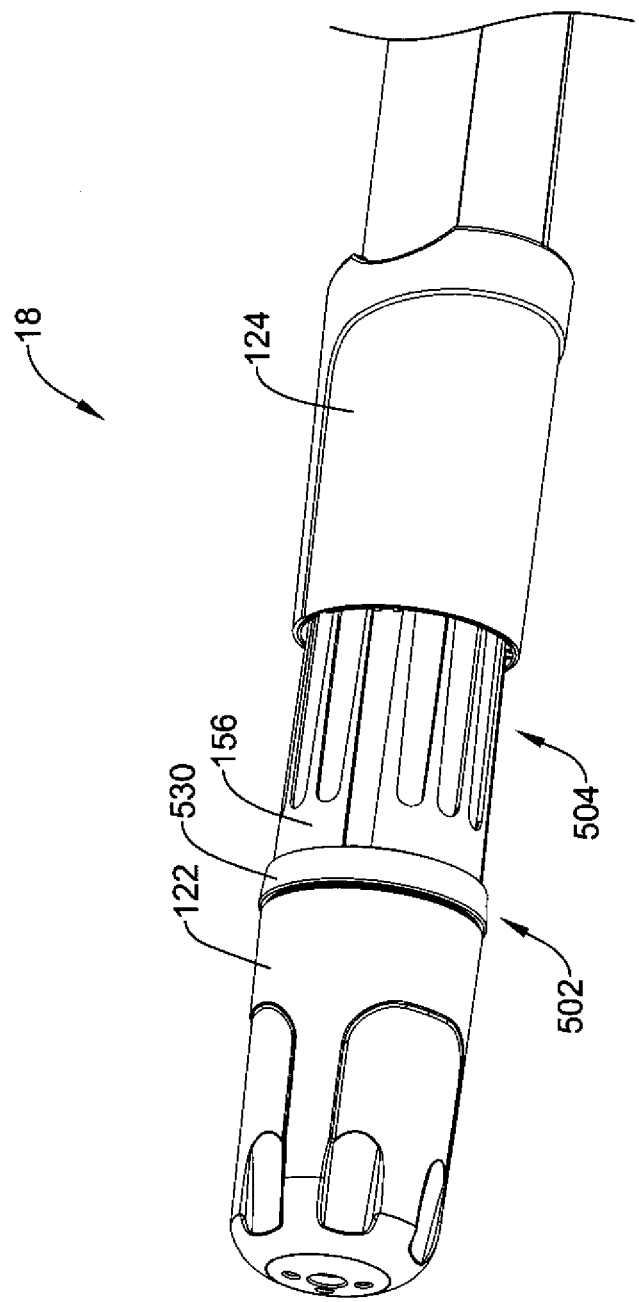

Door 124 may be disposed about distal portion 504 of collar 156. Door 124 may be axially slidable along a longitudinal axis of handle housing 120 between a closed position (e.g., as seen in FIG. 23) in which door 124 substantially covers distal portion 504 of collar 156, a first open position (e.g., as seen in FIG. 24) in which distal portion 504 is partially uncovered, and a second open position (e.g. as seen in FIG. 28) distal of the first open position. In some embodiments, collar 156, control knob 122, and door 124 may be concentrically disposed about the longitudinal axis of handle housing 120.

Figure 32:
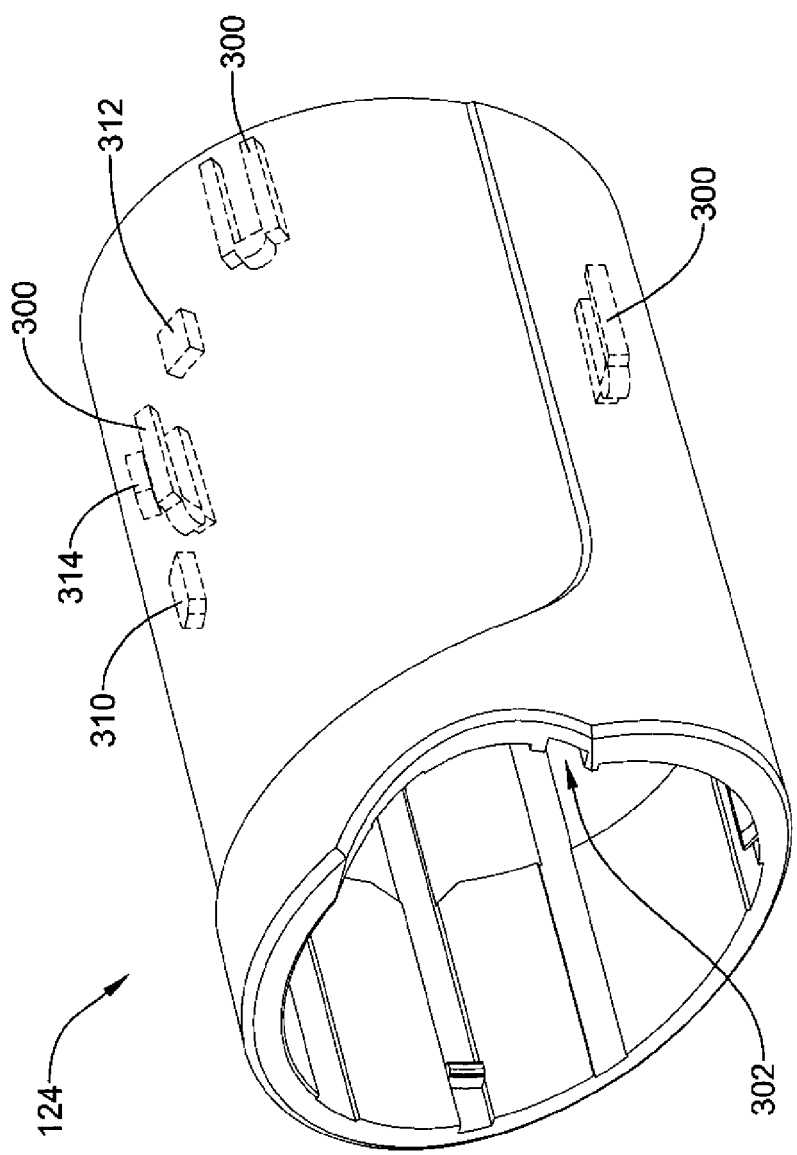
FIG. 32 is a perspective view of the door of FIG. 23.
Figure 32A:
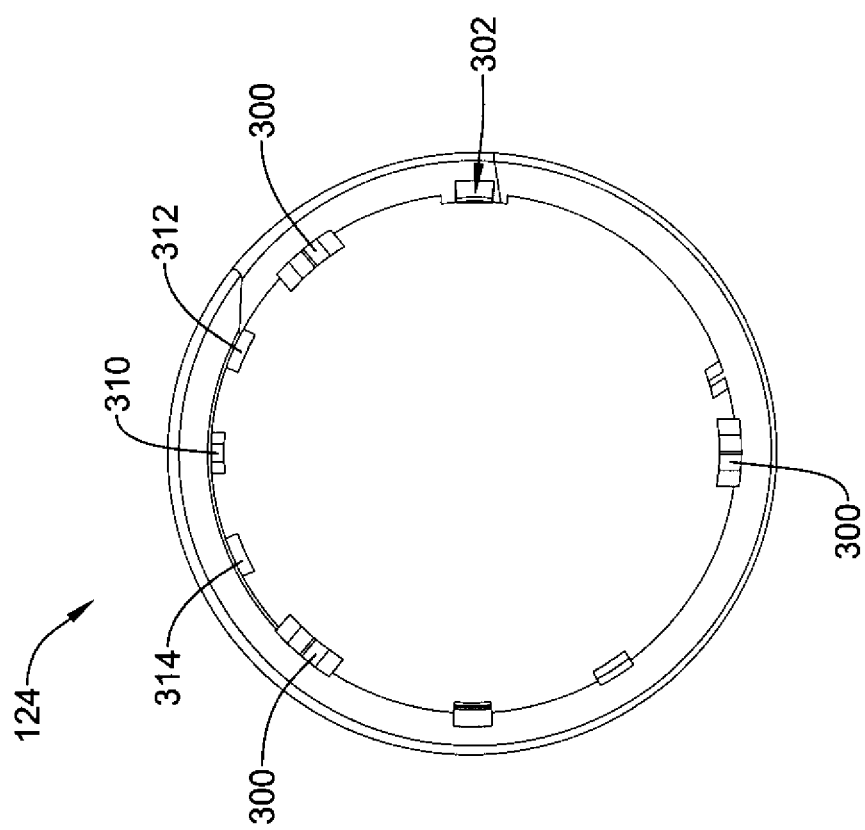
FIG. 32A is a left end view of the door of FIG. 32.

As seen in FIG. 25, handle housing 120 may include at least one guide stop 400 extending radially outward from an outer surface of handle housing 120. Door 124 may include at least one groove 302 in an inner surface thereof (e.g., as seen in FIGS. 32 and 32A), wherein the at least one groove 302 is configured to receive and cooperate with the at least one guide stop 400 to prevent rotation of door 124 relative to handle housing 120 in the closed position. In some embodiments, the at least one groove 302 does not extend the entire length of door 124. Accordingly, when door 124 is translated distally a sufficient distance (e.g., to the first open position), guide stop 400 will exit groove 302, thereby permitting door 124 to rotate relative to the handle housing 120.

Figure 26:
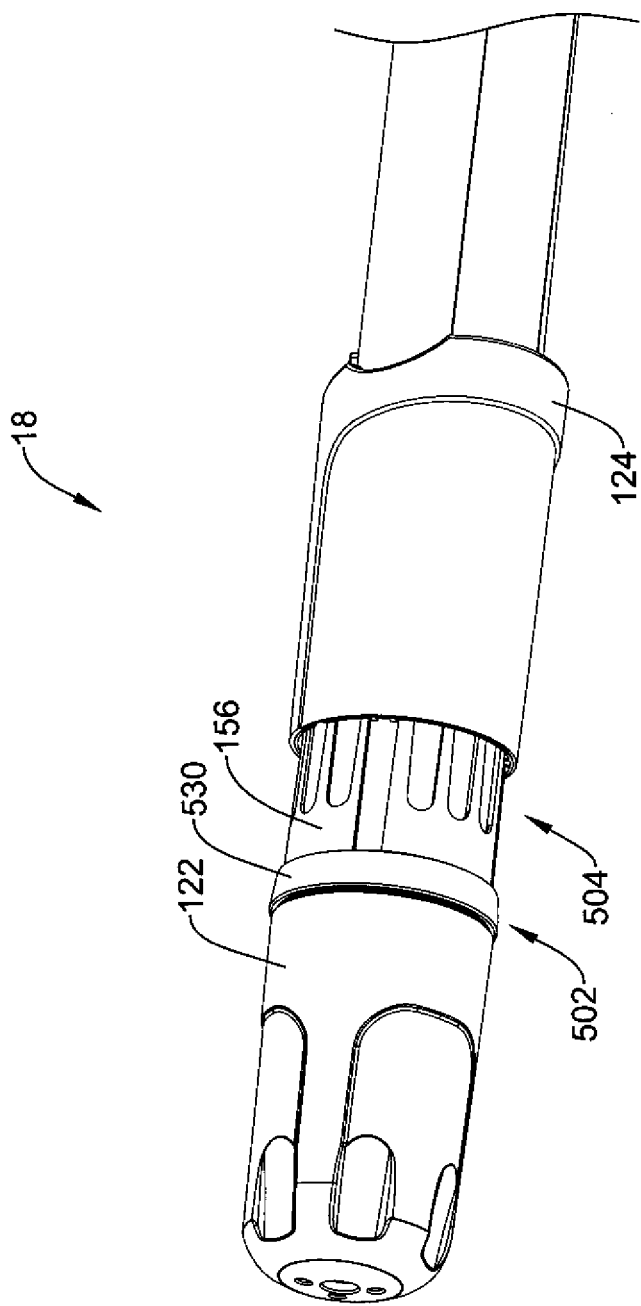
Figure 27:
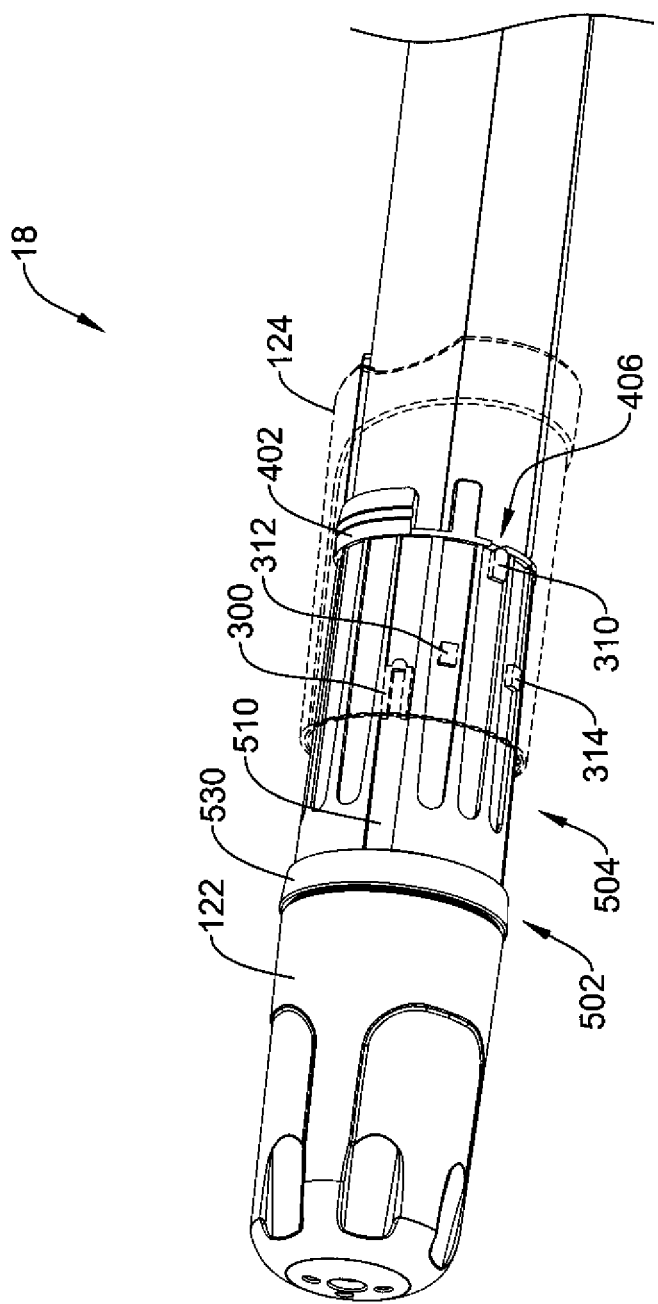

Handle housing 120 may also include a radially-extending transverse ridge 402 disposed about the handle housing 120. A distal end of collar 156 may abut a proximally-facing surface of the ridge 402, as seen in FIG. 25. Door 124 may include a plurality of protruding stops and a plurality of alignment protrusions 300 extending radially inward from an inner surface of door 124. A first protruding stop 310 may abut the proximally-facing surface of ridge 402 in the first open position. A second protruding stop 312 and a third protruding stop 314 may be disposed proximally of the first protruding stop 310 on the inner surface of door 124. Rotation of door 124 in the first open position may translate the first protruding stop 310 radially about handle housing 120 along the proximally-facing surface of ridge 402 (as seen in FIGS. 26-27). Rotation of door 124 in the first open position may move chock 148 and translate first shaft 142 proximally to pull pins 88 and release the push-pull rods 84 from posts 72, as described above.

Figure 29:
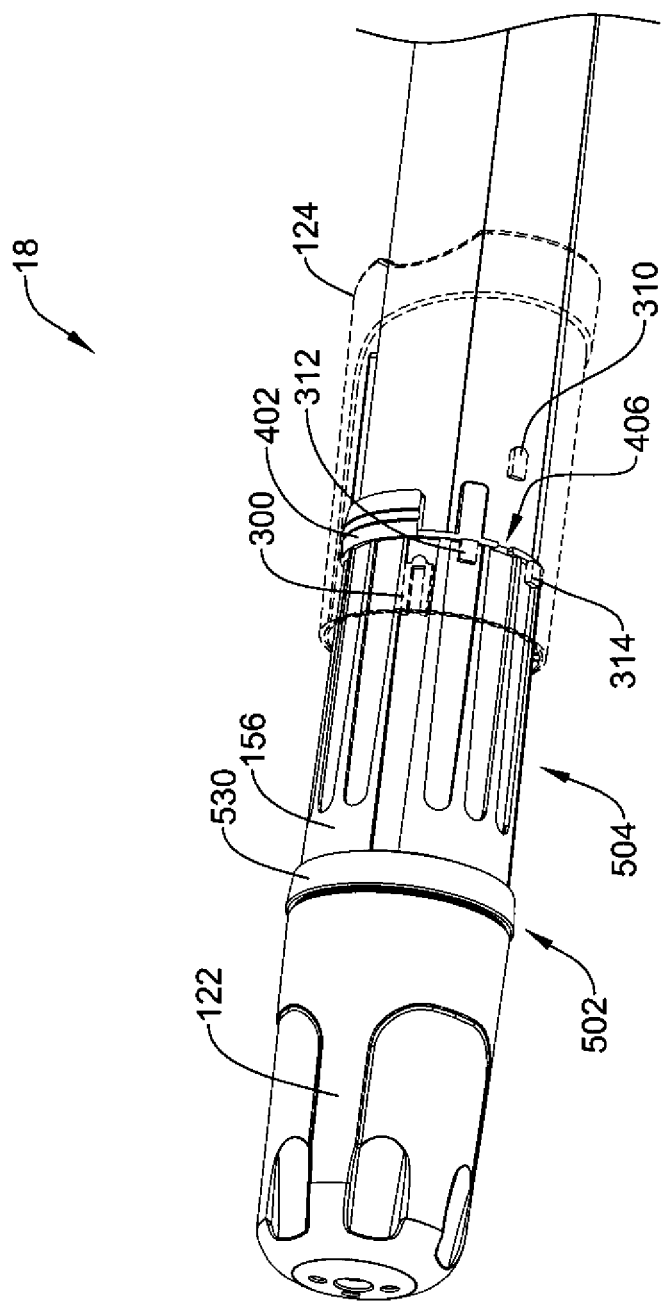

Ridge 402 may include at least one opening 406 extending therethrough along an outer surface of handle housing 120, as seen in FIG. 27. As door 124 is rotated in the first open position, the user/practitioner may apply light distal force to door 124. When door 124 reaches opening 406, first protruding stop 310 may move through opening 406 and door 124 may be further translated distally until second protruding stop 312 and third protruding stop 314 abut the proximally-facing surface of ridge 402 in the second open position (as seen in FIGS. 28-29). In some embodiments, handle housing 120 may include a hard or physical stop that aligns first protruding stop 310 with opening 406, thereby limiting rotation of door 124 in the first open position. This further distal movement of door 124 (and/or the hard or physical stop, if present) may serve as an indicator or reminder for the user/practitioner to verify the positioning of posts 72 and buckles 76 and ensure that proper locking has taken place, prior to withdrawing push-pull rods 84 from posts 72. As long as push-pull rods 84 have not been withdrawn proximally to move collar 80 off of the forked end 104 of the fingers of coupler 78, implant 16 remains secured to three finger coupler 78 and may be re-sheathed and removed if proper locking has failed.

Figure 30:
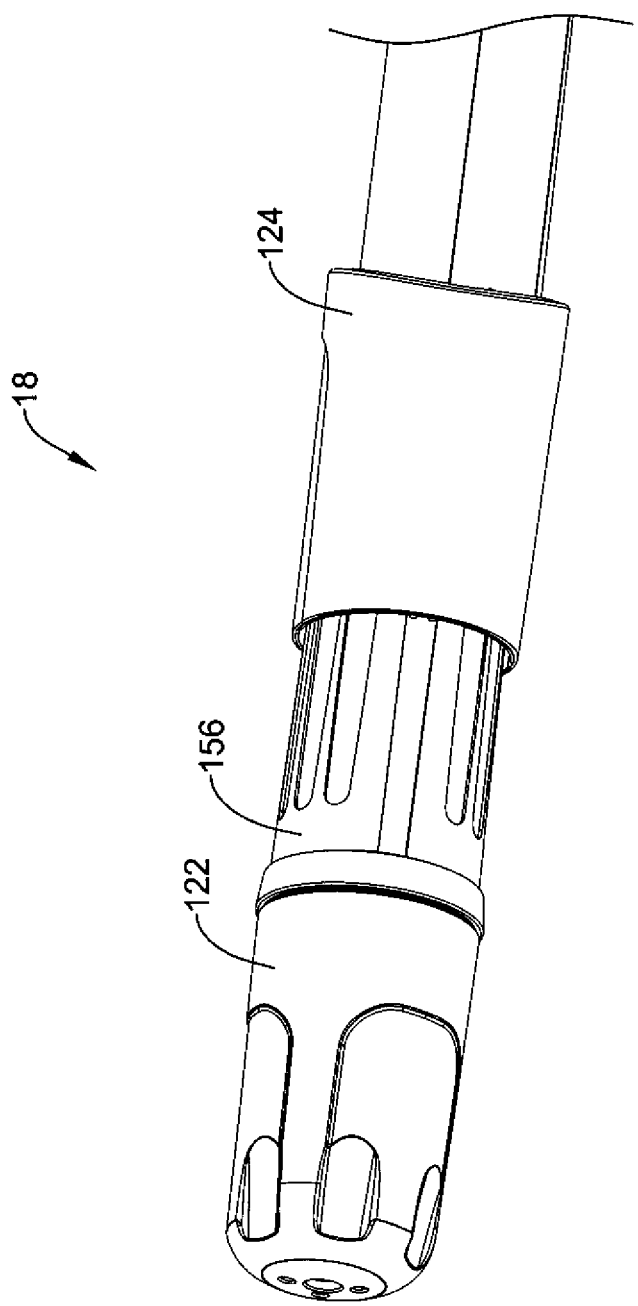
Figure 31:
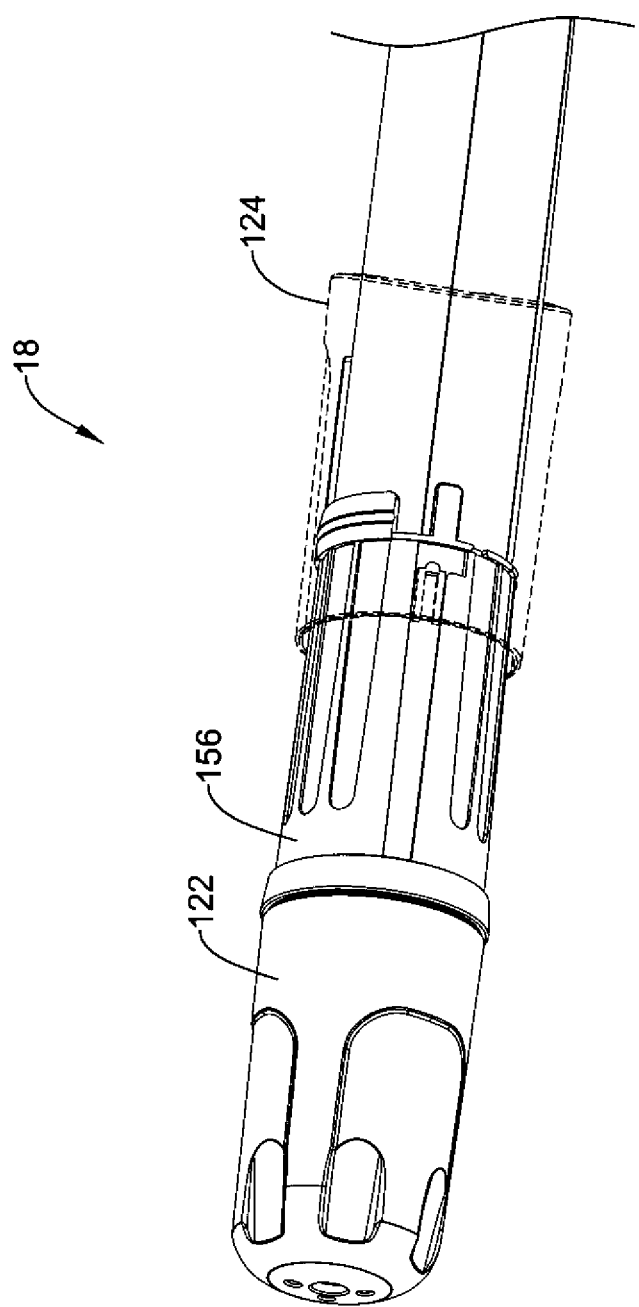

Rotation of door 124 in the second open position (e.g. as seen in FIGS. 30-31) may translate the second protruding stop 312 and the third protruding stop 314 radially about handle housing 120 along the proximally-facing surface of ridge 402. Rotation of door 124 in the second open position also translates second shaft 144 proximally to withdraw push-pull rods 84 from posts 72, thereby releasing implant 16.

In some embodiments, alignment protrusions 300 may generally be longitudinally elongated and of similar size and/or shape as recessed slots 510. Alignment protrusions 300 may engage the plurality of recessed slots 510 in the outer surface of collar 156 to prevent relative rotation between door 124 and collar 156. That is, alignment protrusions 300 engage with slots 510 in a manner that rotatably locks door 124 to collar 156 such that door 124 and collar 156 must rotate together, or in tandem.

Accordingly, door 124 and/or flag member 164 may prevent rotation of collar 156 relative to handle housing 120 when door 124 is in the closed position and/or when flag member 164 is in the engaged configuration. After flag member 164 has been moved proximally to the disengaged configuration, door 124 may be slid distally into the first open position. Collar 156 is free to rotate about handle housing 120 under these conditions. Door 124 and collar 156 cooperate to form a hand grip that may be rotated to move chock 148 and pull pins 88 to release the push-pull rods 84 from posts 72, as described above. The hand grip formed by the cooperation of door 124 and collar 156 provides a wider, larger diameter surface for a user/practitioner to grasp and rotate than collar 156 alone.

The materials that can be used for the various components of system 10 (and/or other systems disclosed herein) and the various tubular members disclosed herein may include those commonly associated with medical devices. For simplicity purposes, the following discussion makes reference to outer sheath 12 and/or inner catheter 14. However, this is not intended to limit the devices and methods described herein, as the discussion may be applied to other similar tubular members and/or components of tubular members or devices disclosed herein.

Outer sheath 12 and/or inner catheter 14 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of outer sheath 12 and inner catheter 14 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10 to achieve the same result.

In some embodiments, a degree of Magnetic Resonance Imaging (MRI) compatibility is imparted into system 10. For example, outer sheath 12 and inner catheter 14, or portions thereof, may be made of a material that does not substantially distort the image and create substantial artifacts (i.e., gaps in the image). Certain ferromagnetic materials, for example, may not be suitable because they may create artifacts in an MRI image. Outer sheath 12 and inner catheter 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of outer sheath 12 and inner catheter 14 that may define a generally smooth outer surface for system 10. In other embodiments, however, such a sheath or covering may be absent from a portion of all of system 10, such that outer sheath 12 and inner catheter 14 may form an outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the system 10 (including, for example, the exterior surface of outer sheath 12 and inner catheter 14) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of outer sheath 12 and inner catheter 14, or other portions of system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof.

Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The following documents are herein incorporated by reference in their entirety:
U.S. Patent Application Pub No. US 2007/0112355,
U.S. Patent Application Pub No. US 2010/0219092,
U.S. Patent Application Pub No. US 2010/0280495,
U.S. patent application Ser. No. 12/578,447, filed on Oct. 13, 2009 and entitled "Medical Devices and Delivery Systems for Delivering Medical Devices",
U.S. Patent Application Ser. No. 61/559,914, filed on Nov. 15, 2011 and entitled "Duel Sterilization Containment Vessel",
U.S. Patent Application Ser. No. 61/559,892, filed on Nov. 15, 2011 and entitled "Improved Bond Between Components of a Medical Device",
U.S. Patent Application Ser. No. 61/559,941, filed on Nov. 15, 2011 and entitled "Medical Device With One Or More Sheathing Transition Members",
U.S. Patent Application Ser. No. 61/559,871, filed on Nov. 15, 2011 and entitled "Medical Device With Nosecone And Nosecone Tube Extension",
U.S. Patent Application Ser. No. 61/558,095, filed on Nov. 10, 2011 and entitled "Direct Connect Flush System",
U.S. Patent Application Ser. No. 61/559,931, filed on Nov. 15, 2011 and entitled "Medical Device With Keyed Locking Structures",
U.S. Patent Application Ser. No. 61/566,615, filed on Dec. 3, 2011 and entitled "Medical Device Handle",
U.S. Patent Application Ser. No. 61/577,845, filed on Dec. 20, 2011 and entitled "Medial Device Handle",
U.S. Patent Application Ser. No. 61/577,880, filed on Dec. 20, 2011 and entitled "Post Lock",
U.S. Patent Application Ser. No. 61/577,891, filed on Dec. 20, 2011 and entitled "Heart Valve Replacement Catheter", and
U.S. Patent Application Ser. No. 61/543,521, filed on Oct. 5, 2011 and entitled "Profile Reduction Seal", It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:
1. A medical device handle, comprising:
an elongated handle housing having a radially-extending transverse ridge disposed about its circumference, wherein the transverse ridge further includes an opening extending therethrough along an outer surface of the handle housing;
   a collar disposed about a proximal portion of the handle housing and rotatable relative to the handle housing, a distal end of the collar abutting a proximally-facing surface of the transverse ridge;
   a control knob disposed about a proximal end of the collar at a proximal end of the handle housing and rotatable relative to the handle housing; and
   a slidable door disposed about a distal portion of the collar,
wherein the slidable door is rotatably locked to the collar,
wherein the slidable door is slidable between a closed position wherein the slidable door substantially covers the distal portion of the collar and is engaged with the handle housing to prevent rotation of the slidable door relative to the handle housing, and a first open position wherein the distal portion of the collar is partially uncovered and the slidable door is disengaged from the handle housing such that rotation of the slidable door relative to the handle housing is permitted.

2. The medical device handle of claim 1, wherein the collar is selectively rotatable about the handle housing.

3. The medical device handle of claim 1, wherein the control knob is selectively rotatable about a longitudinal axis of the handle housing.

4. The medical device handle of claim 1, wherein the collar includes a radially-extending transverse flange portion disposed about a slidable door abuts central portion of the collar;
   wherein the flange portion spaces the control knob longitudinally from the slidable door.

5. The medical device handle of claim 1, wherein the collar includes a plurality of recessed slots in an outer surface thereof, and the slidable door includes a plurality of alignment protrusions extending radially inward from an inner surface thereof;
   wherein the plurality of alignment protrusions engage the plurality of recessed slots and prevent relative rotation between the collar and the slidable door.

6. The medical device handle of claim 1, wherein in the first open position, a first protruding stop extending radially inward from an inner surface of the slidable door abuts the proximally-facing surface of the transverse ridge.

7. The medical device handle of claim 6, wherein rotation of the slidable door in the first open position translates the first protruding stop along the proximally-facing surface of the transverse ridge.

8. The medical device of claim 7, wherein rotation of the slidable door in the first open position translates a first shaft longitudinally within the handle housing.

9. The medical device handle of claim 7, wherein the slidable door further includes a second protruding stop extending radially inward from an inner surface of the slidable door and a third protruding stop extending radially inward from an inner surface of the slidable door, and the slidable door is further slidable to a second open position distal of the first open position;
   wherein the first protruding stop passes distally through the opening in the transverse ridge and the slidable door is further translated distally until the second and third protruding stops abut the proximally-facing surface of the transverse ridge in the second open position.

10. The medical device of claim 9, wherein rotation of the slidable door in the second open position translates the second and third protruding stops along the proximally-facing surface of the transverse ridge.

11. The medical device of claim 10, wherein rotation of the slidable door in the second open position translates a second shaft longitudinally within the handle housing.

12. The medical device handle of claim 1, wherein the handle housing includes at least one guide stop extending radially outward from an outer surface of the handle housing;
   wherein the slidable door includes at least one groove in an inner surface thereof;
   wherein the at least one groove is configured to engage the at least one guide stop to prevent rotation of the slidable door in the closed position.

13. The medical device handle of claim 1, further comprising an actuator for actuating the medical device disposed distally of the medical device handle, the actuator being disposed within the handle housing and translating longitudinally in response to rotation of the control knob.

14. The medical device handle of claim 13, wherein the actuator for actuating includes an interlocking element extending radially outward from a longitudinal axis, the interlocking element having an engaged configuration and a disengaged configuration;
   wherein in the engaged configuration, the interlocking element physically prevents the collar from rotating; and
   wherein in the disengaged configuration, the interlocking element permits the collar to rotate.

\* \* \* \* \*